(12) United States Patent
Nielsen et al.

(10) Patent No.: US 12,369,853 B2
(45) Date of Patent: Jul. 29, 2025

(54) OSTOMY SYSTEM FOR PREDICTING A SITE OF LEAKAGE

(71) Applicant: Coloplast A/S, Humlebaek (DK)

(72) Inventors: Finn Nielsen, Copenhagen (DK); Torben Holst Nielsen, Hedehusene (DK)

(73) Assignee: Coloplast A/S, Humlebaek (DK)

( * ) Notice: Subject to any disclaimer, the term of this patent is extended or adjusted under 35 U.S.C. 154(b) by 522 days.

(21) Appl. No.: 17/786,538

(22) PCT Filed: Dec. 18, 2020

(86) PCT No.: PCT/DK2020/050382
§ 371 (c)(1),
(2) Date: Jun. 17, 2022

(87) PCT Pub. No.: WO2021/121517
PCT Pub. Date: Jun. 24, 2021

(65) Prior Publication Data
US 2023/0030622 A1    Feb. 2, 2023

(30) Foreign Application Priority Data
Dec. 18, 2019    (DK) .............. PA 2019 70787

(51) Int. Cl.
*A61F 5/44*    (2006.01)
*A61B 5/00*    (2006.01)
*A61F 5/443*    (2006.01)

(52) U.S. Cl.
CPC .......... *A61B 5/4851* (2013.01); *A61F 5/4404* (2013.01); *A61F 5/443* (2013.01)

(58) Field of Classification Search
CPC .... A61B 5/4851; A61F 13/42; A61F 2013/42; A61F 5/44; A61F 5/4404; A61F 5/443; A61F 5/445; A61M 1/3656; A61M 1/3658
See application file for complete search history.

(56) References Cited

U.S. PATENT DOCUMENTS

| 6,171,289 B1 | 1/2001 | Millot et al. |
| 2017/0340474 A1 | 11/2017 | Thirstrup et al. |

(Continued)

FOREIGN PATENT DOCUMENTS

| DE | 19953062 A1 | 5/2000 |
| WO | 2019120431 A1 | 6/2019 |

(Continued)

*Primary Examiner* — Susan S Su
*Assistant Examiner* — Erin A Kim
(74) *Attorney, Agent, or Firm* — Coloplast Corp., Coloplast A/S; Nick Baumann

(57) ABSTRACT

An ostomy system, a sensor assembly (310) for an ostomy appliance of an ostomy system, and a method related to the ostomy system is disclosed. The ostomy appliance comprises a first adhesive layer (80), a sensor assembly (310), and a monitor device. The sensor assembly (310) comprises a first sensor (311) at least partly encircling the centre point and a second sensor (312) at least partly encircling the first sensor (311). The first sensor (311) comprises at least a primary sensing segment (311a) arranged in a primary sector (310A) of the sensor assembly and a secondary sensing segment (311b) arranged in a secondary sector (310B). The monitor device is configured to determine a main sector (310M) wherein liquid has been detected by the primary and/or secondary sensing segment (311a/311b), respectively, and to indicate a site of leakage from the ostomy appliance based on at least the main sector (310M).

20 Claims, 9 Drawing Sheets

(56) References Cited

U.S. PATENT DOCUMENTS

2019/0133812 A1* 5/2019 Seres ............... A61F 5/443
2019/0192332 A1   6/2019 Hansen et al.
2021/0386368 A1* 12/2021 Carlsson ........... A61F 5/443

FOREIGN PATENT DOCUMENTS

| WO | 2019120437 A1 | 6/2019 |
| WO | 2019120445 A1 | 6/2019 |
| WO | 2019120449 A1 | 6/2019 |
| WO | 2019120453 A1 | 6/2019 |

* cited by examiner

OSTOMY SYSTEM FOR PREDICTING A SITE OF LEAKAGE

The present disclosure relates to an ostomy system and related methods and in particular to an ostomy system configured to predict a site of leakage from an ostomy appliance. An ostomy system, and devices of the ostomy system are disclosed. In particular, the present disclosure relates to a monitor device configured to indicate a site of leakage from an ostomy appliance based on sensor data.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1A:
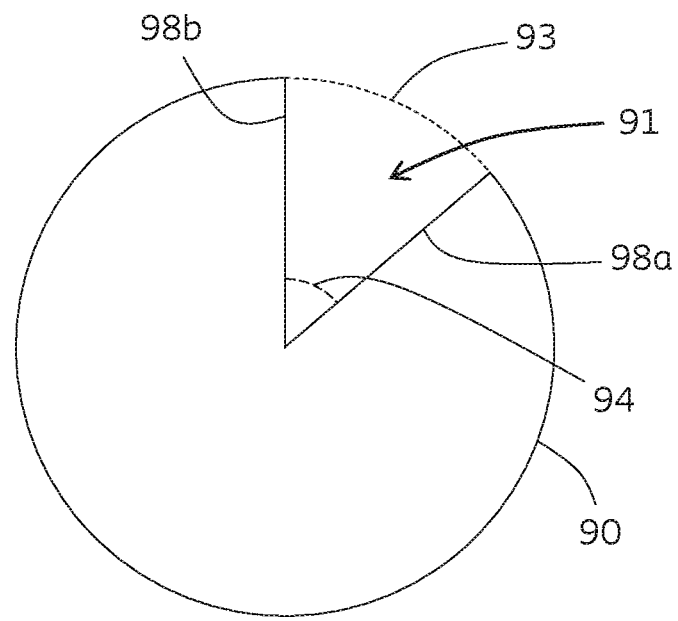
FIG. 1A illustrates a circle according to Euclidean geometry.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g., "stomal", "ostomies" etc. Also, the solid and liquid wastes emanating from the stoma may be referred to as both stomal "output," "waste(s)," "liquids," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

A radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure provides an ostomy system configured to predict a site of leakage from an ostomy appliance, a sensor assembly for such an ostomy system, and a method for predicting a site of leakage from an ostomy appliance.

In a first aspect of the invention, an ostomy system is disclosed. The ostomy system is configured to predict a site of leakage from an ostomy appliance. The ostomy system comprises the ostomy appliance and a monitor device. The ostomy appliance comprises a first adhesive layer, a sensor assembly, and a monitor device. The first adhesive layer comprises a distal side including a distal surface and a proximal side including a proximal surface. The proximal surface is configured for attachment to the skin surface of a user. The first adhesive layer comprises a stomal opening with a centre point. The sensor assembly is arranged on the distal side of the first adhesive layer. In embodiments, the sensor assembly is arranged on the proximal surface. The sensor assembly comprises a first sensor at least partly encircling the centre point and a second sensor at least partly encircling the first sensor. The first sensor and the second sensor are arranged to facilitate detection of liquid on the proximal surface of the first adhesive layer. The first sensor comprises at least a primary sensing segment arranged in a primary sector of the sensor assembly and a secondary sensing segment arranged in a secondary sector of the sensor assembly. The monitor device is configured to detect liquid at the primary sensing segment and/or at the secondary sensing augment of the first sensor and to detect liquid at the second sensor. Further, the monitor device is configured to determine a main sector of the sensor assembly comprising the primary and/or secondary sector wherein liquid has been detected by the primary and/or secondary sensing segment, respectively, and to indicate a site of leakage from the ostomy appliance based on at least the main sector.

The present disclosure relates to an ostomy system and devices thereof, such as an ostomy appliance, a base plate for an ostomy appliance, a sensor patch for application to a baseplate, a monitor device, and optionally one or more accessory devices. Further, methods related to the ostomy system and devices thereof are disclosed. An accessory device (also referred to as an external device) can be a mobile phone or other handheld device. In embodiments, an accessory device is a personal electronic device, e.g., a wearable, such as a watch or other wrist-worn electronic device. An accessory device can be a docking station. In embodiments, the docking station is configured to electrically and/or mechanically couple the monitor device to the docking station. In embodiments, the docking station is configured for charging a battery of the monitor device and/or configured for transferring data between the monitor device and the docking station. The ostomy system can comprise a server device. In embodiments, the server device is operated and/or controlled by the ostomy appliance manufacturer and/or a service centre.

The present disclosure provides an ostomy system and devices thereof, such as an ostomy appliance, a base plate for an ostomy appliance, a sensor patch for application to a base plate, a monitor device, and optionally one or more accessory devices which either alone or together facilitate reliable determination of the nature, severity, and rapidness of moisture propagation in the adhesive material provided for attaching the base plate and/or sensor patch to the skin surface of a user. Depending on the nature of the pattern of moisture propagation in the adhesive, the ostomy system and devices thereof enable providing information to the user about the type of failure, such as adhesive failure patterns, and in turn enable providing an indication to the user of the severity and thus the remaining time frame for replacing the ostomy appliance without experiencing severe leakage and/or skin damage.

In embodiments, the ostomy appliance includes a base plate, such as a monolithic, one-piece base plate, e.g., integrated with a sensor assembly part, or a separate sensor assembly part, such as a sensor assembly part to be subsequently applied to a base plate. In embodiments, the sensor assembly part is a sensor patch for application to the base plate, such as the proximal surface of the base plate. Thereby, an arbitrary base plate, such as a conventional base plate provided with the sensor patch, can achieve the features as described herein. Features as described with respect to sensing/monitoring capabilities of the base plate herein can be provided by a sensor assembly of a sensor patch to be applied to a base plate, e.g., by the user, and vice versa. In embodiments, the sensor patch is adapted to adhere to a base plate. In embodiments, the sensor patch comprises a first adhesive layer adapted to adhere to the skin surface of a user.

In embodiments, a method of attaching a base plate having sensing capabilities, e.g., through the provision of a sensor patch, to a user's stoma and/or skin surrounding the stoma, such as the peristomal skin area, comprises attaching the sensor patch to a base plate and attaching the base plate, i.e. together with the attached sensor patch, to the user's stoma and/or skin surrounding the stoma, such as the peristomal skin area. Alternatively, the method of attaching the base plate to the user's stoma and/or skin surrounding the stoma comprises attaching the sensor patch to the user's stoma and/or skin surrounding the stoma and attaching the base plate to the user's stoma and/or skin surrounding the stoma above the attached sensor patch, i.e., on a distal surface of the sensor patch.

In embodiments, the ostomy appliance comprises a base plate and an ostomy pouch (also referred to as an ostomy bag). The ostomy appliance can be a colostomy appliance, an ileostomy appliance, or a urostomy appliance. In embodiments, the ostomy appliance is a two-part ostomy appliance, i.e., the base plate and the ostomy pouch are releasably coupled, e.g., with a mechanical and/or an adhesive coupling, e.g., to allow that a plurality of ostomy pouches can be utilized (exchanged) with one base plate. Further, a two-part ostomy appliance can facilitate correct application of the base plate to skin, e.g., to an improved user sight of the stomal region. In embodiments, the ostomy appliance is a one-part ostomy appliance, i.e., the base plate and the ostomy pouch are fixedly attached to each other. The base plate is configured for coupling to a user's stoma and/or skin surrounding the stoma, such as a peristomal skin area.

In embodiments, the ostomy system comprises a base plate or a sensor patch for application to a base plate. In embodiments, parts of the ostomy system are incorporated into a base plate or a sensor patch for application to a base plate. In embodiments, the first adhesive layer of the ostomy system is a first adhesive layer of a base plate or a sensor patch for attachment to a base plate. In embodiments, the first adhesive layer and the sensor assembly of the ostomy system are incorporated into a base plate or sensor patch to provide such with the ability to indicate a site of leakage. In embodiments, the ostomy system provides a base plate and/or a sensor patch with the ability to indicate a site of leakage from an ostomy appliance, e.g., from the base plate.

The ostomy appliance comprises a first adhesive layer with a proximal side including a proximal surface configured for attachment to the skin surface of a user and a distal side including a distal surface. In embodiments, the first adhesive layer of the ostomy system is provided as part of a base plate or a sensor patch. In embodiments, the base plate and/or the sensor patch comprises the first adhesive layer and the sensor assembly of the ostomy system according to the first aspect of the invention. The first adhesive layer comprises a stomal opening, such as a first adhesive stomal opening, with a centre point, or is at least prepared for forming a stomal opening with a centre point.

During use, the first adhesive layer adheres to the user's skin (peristomal area) and/or to additional seals, such as sealing paste, sealing tape and/or sealing ring. Thus, in embodiments, the first adhesive layer is configured for attachment to the skin surface of a user, e.g., for attachment of a base plate and/or the sensor patch to the skin surface of a user. A first adhesive layer, e.g., when embodied in a base plate and/or a sensor patch, according to the present disclosure enables detection of presence of liquid or output on the proximal surface of the first adhesive layer (between a skin surface of the user, such as the peristomal skin area, and the proximal surface of the first adhesive layer).

In embodiments, the first adhesive layer is made of a first composition. In embodiments, the first composition comprises one or more polyisobutenes and/or styrene-isoprene-styrene. In embodiments, the first composition comprises one or more hydrocolloids. In embodiments, the first composition comprises one or more water soluble or water swellable hydrocolloids. In embodiments, the first composition is a pressure sensitive adhesive composition suitable for medical purposes comprising a rubbery elastomeric base and one or more water soluble or water swellable hydrocolloids. In embodiments, the first composition comprises one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. For example, the styrene copolymer can be a styrene-butadiene-styrene block copolymer or a styrene-isoprene-styrene block copolymer. Preferably, one or more styrene-isoprene-styrene (SIS) block type copolymers are employed. The amount of styrene block-copolymer can be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids, and synthetic hydrocolloids. The first composition can comprise 20-60% hydrocolloids. A preferred hydrocolloid is carboxymethyl cellulose (CMC). Optionally, the first composition can contain other components, such as fillers, tackifiers, plasticizers, and/or other additives.

The first adhesive layer can have a substantially uniform thickness. The first adhesive layer can have a thickness in the range from 0.1 mm to 1.5 mm, e.g., in the range from 0.2 mm to 1.2 mm, such as 0.8 mm or 1.0 mm. The first adhesive layer can have a primary thickness in a primary part of the first adhesive layer, e.g., in a primary region within a primary radial distance or in a primary radial distance range from the centre point of the stomal opening. The primary thickness can be in the range from 0.2 mm to 1.5 mm. such as about 1.0 mm. The primary radial distance can be in the range from 20 mm to 50 mm, such as in the range from 25 mm to 35 mm, e.g., 30 mm. The first adhesive layer can have a secondary thickness in a secondary part of the first adhesive layer, e.g., in a secondary region outside a secondary radial distance or in a secondary radial distance range from the centre point of the stomal opening. The secondary thickness can be in the range from 0.2 mm to 1.0 mm, such as about 0.5 mm. The secondary radial distance can be in the range from 20 mm to 50 mm, such as in the range from 25 mm to 35 mm, e.g., 30 mm.

In embodiments, the ostomy system comprises a second layer, e.g., a second layer provided as part of a base plate and/or sensor patch of the ostomy system. In embodiments, the second layer is an adhesive layer. In embodiments, the second layer has a second radial extension that is larger than a first radial extension of the first adhesive layer at least in a first angular range of the base plate and/or the sensor patch. Accordingly, a part of a proximal surface of the second layer can be configured for attachment to the skin surface of a user. The part of a proximal surface of the second layer configured for attachment to the skin surface of a user is also denoted the skin attachment surface of the second adhesive layer. The second layer can have a stomal opening, such as a second layer stomal opening and/or a second adhesive stomal opening, with a centre point. In embodiments, the centre point of the second layer is coinciding (aligned) with the centre point of the first adhesive layer.

In embodiments, the second adhesive layer is made of a second composition. In embodiments, the second composition comprises one or more polyisobutenes and/or styrene-isoprene-styrene. In embodiments, the second composition comprises one or more hydrocolloids. In embodiments, the second composition comprises one or more water soluble or water swellable hydrocolloids. In embodiments, the second composition is a pressure sensitive adhesive composition suitable for medical purposes comprising a rubbery elastomeric base and one or more water soluble or water swellable hydrocolloids. In embodiments, the second composition comprises one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. For example, the styrene copolymer can be a styrene-butadiene-styrene block copolymer or a styrene-isoprene-styrene block copolymer. Preferably, one or more styrene-isoprene-styrene (SIS) block type copolymers are employed. The amount of styrene block-copolymer can be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids, and synthetic hydrocolloids. The second composition can comprise 20-60% hydrocolloids. A preferred hydrocolloid is carboxymethyl cellulose (CMC). Optionally, the second composition can contain other components, such as fillers, tackifiers, plasticizers, and/or other additives.

Different ratio of contents can change properties of the first and/or second adhesive layers. In embodiments, the second adhesive layer and the first adhesive layer have different properties. In embodiments, the second adhesive layer (second composition) and the first adhesive layer (first composition) have different ratios of polyisobutenes, styrene-isoprene-styrene, and/or hydrocolloids. For example, the second adhesive layer can provide a stronger attachment to the skin compared to attachment to the skin provided by the first adhesive layer. Alternatively, or additionally, the second adhesive layer can be thinner than the first adhesive layer. Alternatively, or additionally, the second adhesive layer can be less water and/or sweat absorbing than the first adhesive layer. Alternatively, or additionally, the second adhesive layer can be less mouldable than the first adhesive layer. In embodiments, the second adhesive layer provides a second barrier against leakage.

The second layer can have a substantially uniform thickness. The second layer can have a thickness in the range from 0.1 mm to 1.5 mm, e.g., in the range from 0.2 mm to 1.0 mm, such as 0.5 mm, 0.6 mm, or 0.7 mm.

The ostomy appliance comprises a sensor assembly. In embodiments, the sensor assembly is arranged on the distal side of the first adhesive layer, such as on the distal surface of the first adhesive layer, such as attached to the distal surface. In embodiments, the sensor assembly is attached to the proximal surface of the first adhesive layer. In embodiments, the sensor assembly is attachable to the distal surface or the proximal surface of the first adhesive layer.

The sensor assembly comprises at least two sensors; a first sensor and a second sensor. In embodiments, the sensor assembly comprises two, three, four, five, or six sensors. In embodiments, the sensor assembly comprises more than six sensors. The sensors are arranged to facilitate detection of liquid on the proximal surface of the first adhesive layer, e.g., on the proximal surface of a base plate and/or a sensor patch incorporating parts of the ostomy system. Detection of liquid can be indicative of output present in the interface between the first adhesive layer and the skin surface, which eventually can cause leakage from the first adhesive layer, i.e., output escaping the base plate and causing distress to the user. Thus, it is desired to provide a warning before such leakage. By liquid is meant in particular all types of output emanating from a stoma, varying from highly viscous output to solid output. Further, in embodiments, by liquid is meant moisture, such as moisture absorbed by the first adhesive layer. Thus, in the following, a reference to liquid is meant at least a reference to all types of output. In the following, whenever referring to an interface is meant the interface between the first adhesive layer and the (peristomal) skin surface, unless otherwise specified.

The first sensor of the sensor assembly at least partly encircles the centre point of the first adhesive layer. By encircling the centre point is meant that the first sensor encloses the centre point, such as the stomal opening, when seen in a direction normal to the plane comprising the sensor and the centre point. Thus, the first and second sensor is, in embodiments, provided in the same geometrical plane. In embodiments, the sensor assembly comprises a centre point. In embodiments, the centre point of the sensor assembly is aligned/coincides with the centre point of the first adhesive layer. Thus, the first sensor is arranged to facilitate detection of liquid/output emanating from the stoma in any given direction. In embodiments, the first sensor is circular about the centre point. In embodiments, the first sensor is circular, such as concentric, about the stomal opening. In embodiments, the first sensor encircles the centre point. In embodiments, the first sensor is arranged at a first radial distance from the centre point. In embodiments, the first sensor is non-circular but enclosing the centre point and/or the stomal opening. By at least partly encircling is meant that the first sensor substantially encloses the entire space about the centre point/stomal opening, but that a small sector, such as up to 15° of a circle, can be left uncovered in order to provide an outside connection to the sensor, e.g., to allow the first sensor to extend into a monitor interface allowing connection of the sensor to a monitor device. Thus, in embodiments, the sensor assembly comprises a first sensor substantially encircling the centre point and/or the stomal opening. In embodiments, by at least partly encircling the centre point is meant that the first sensor encircles at least 330° of the centre point, such as 335°, 340°, 345°, 350°, 355°, or 359°.

In embodiments, the second sensor of the sensor assembly at least partly encircles the first sensor. By encircling the first sensor is meant that the second sensor encloses the first sensor. In embodiments, the second sensor is concentric about the first sensor. Thus, the second sensor is arranged to facilitate detection of liquid/output having passed by the first sensor when seen in a radial direction from the centre point. In embodiments, the second sensor is circular about the first sensor. In embodiments, the second sensor encircles the first sensor. In embodiments, the second sensor is non-circular but enclosing the first sensor. By at least partly encircling is meant that the second sensor in general encloses the entire space about the first sensor, but that a small sector, such as 1-15° of a circle, can be left uncovered in order to provide an outside connection to the sensor, e.g., to allow the second sensor to extend into a monitor interface allowing connection of the sensor to a monitor device, or to allow the first sensor to pass by the second sensor without causing crossing electrodes. Thus, in embodiments, the sensor assembly comprises a second sensor substantially encircling the first sensor. In embodiments, by at least partly encircling the centre point is meant that the second sensor encircles at least 330° of the first sensor, such as 335°, 340°, 345°, 350°, 355°, or 359°. In embodiments, the second sensor is arranged at a second radial distance from the centre point, the second radial distance being greater than the first radial distance. In embodiments, the first sensor and the second sensor are separated by a first distance. In embodiments, the first distance is between 5 mm and 50 mm, such as 10 mm, 15 mm, 18 mm, 20 mm, 22 mm, 25 mm, 27 mm, 28 mm, 30 mm, 35 mm, 40 mm, or 45 mm.

By providing multiple sensors/sensing segments, different regions of the first adhesive layer can be covered by detection means. In embodiments, a sensor/sensing segment is an electronic component configured to—e.g., in combination with a power source, e.g., of a monitor device—provide a signal indicative of liquid as previously described. In embodiments, a sensor comprises one or more electrodes.

The first sensor comprises at least a primary sensing segment arranged in a primary sector of the sensor assembly and a secondary sensing segment arranged in a secondary sector of the sensor assembly. In embodiments, the first sensor of the sensor assembly comprises two or more sensing segments, such as two, three, four, five, or six sensing segments. Thus, the first sensor is divided into sensing segments, each covering a sector/angle space about the stoma. Thereby, the sensing segments can provide directional information on the propagation and/or presence of liquid. In embodiments, the sensing segments of the first sensor are able to detect presence of liquid independently of each other. In embodiments, the sensing segments are distributed circularly about the centre point/stomal opening of the first adhesive layer. In embodiments, the sensing segments are non-overlapping when seen in a radial direction from the centre point.

In embodiments, the second sensor does not comprise sensing segments. In embodiments, the second sensor is a substantially circular and/or continuous sensor not comprising means (e.g., sensing segments) for distinguishing where about the stoma liquid is present. In embodiments, the second sensor is configured to detect liquid at any angle about the stoma. In embodiments, the second sensor cannot provide directional information on the propagation and/or presence of liquid. Rather, in such embodiments, the second sensor is a simple sensor merely configured to detect presence of liquid circularly about the stoma.

In embodiments, the primary sensing segment and the secondary sensing segment define a primary sector and a secondary sector, respectively. In embodiments, a sector relates to a certain space/region of the sensor assembly or the proximal surface of the first adhesive layer. Thus, in the following, a sector of the sensor assembly can be translated onto (the proximal surface of) the first adhesive layer, such as a first adhesive layer of a base plate and/or sensor patch incorporating the sensor assembly of the ostomy appliance. Thus, when discussing a presence of liquid in a primary sector of the sensor assembly, the discussion is equally applicable to the presence of liquid in a primary sector of (the proximal surface of) the first adhesive layer.

The primary sensing segment and the secondary sensing segment are configured to facilitate detection of liquid and/or moisture content in their respective vicinity, such as upon contact with liquid/moisture. The primary sensing segment is configured to facilitate detection of liquid in the primary sector and the secondary sensing segment is configured to facilitate detection of liquid in the secondary sector.

In embodiments, the primary sector is defined by two radii extending radially away from the centre point of the sensor assembly and a primary angle between the two radii. In embodiments, the secondary sector is defined by two radii radially extending radially away from the centre point of the sensor assembly and a secondary angle between the two radii. In embodiments, the primary and/or secondary angles are central angles of the respective sectors according to definitions in Euclidean geometry. In embodiments, at least one of the radii defining the primary sector is coinciding with at least one radii defining the secondary sector, thereby making the primary sector and the secondary sector neighbouring. In embodiments, the sensor assembly extends substantially circularly about the centre point and hence resembles a disk. In embodiments, a sector of the sensor assembly resembles a sector of a disk/circle as defined in (Euclidean) geometry. In embodiments, a sector of the sensor assembly is a portion of the sensor assembly enclosed by two radii and an arc, the two radii being separated by a central angle. In embodiments, the arc of the sector is a part of the periphery of the sensor assembly or a part of the periphery of the first adhesive layer. In embodiments, a sector of the sensor assembly is defined by two radii separated by a central angle and extending to infinity, i.e., in embodiments, a sector is not delimited by an arc. In embodiments, a sector of the sensor assembly is an arbitrarily-shaped region of the sensor assembly.

In embodiments, the sensors of the sensor assembly are arranged/configured to detect liquid in different sectors, such that it is possible to communicate to the user and/or HCP where about the stoma liquid/output is present.

In embodiments, the sensor assembly is configured to detect presence of liquid, such as output, on the proximal surface of the first adhesive layer and/or moisture content in the first adhesive layer in three or more sectors.

In embodiments, the shape of the primary sensing segment resembles an arc of a circle. In embodiments, the primary sensing segment defines a primary sector of the sensor assembly. In embodiments, the primary sensing segment is arranged between two radii. In embodiments, the primary sector is arranged in a primary angle space from the centre point of the first adhesive layer. In embodiments, the primary sector spans a primary (central) angle in the range from 45° to 315°, such as in the range from 45° to 135°. In embodiments, the primary angle depends on the number of (primary, secondary, etc.) sectors/sensing segments of the sensor assembly (and hence of the base plate and/or the sensor patch). For example, the primary angle of the primary sector can be about 180°±15°, e.g., for a base plate and/or a sensor patch with two or more sectors. The primary angle of the primary sector can be about 120°±15°, e.g., for a base plate and/or a sensor patch with two, three, or more sectors. The primary angle of the primary sector can be about 90°±15°, e.g., for a base plate and/or a sensor patch with two, three, four, or more sectors.

In embodiments, the shape of the secondary sensing segment resembles an arc of a circle. In embodiments, the secondary sensing segment defines a secondary sector of the circle comprising the arc. In embodiments, the secondary sensing segment is arranged between two radii. In embodiments, the secondary sector is arranged in a secondary angle space from the centre point of the first adhesive layer. In embodiments, the secondary sector spans a secondary angle in the range from 45° to 315°, such as in the range from 45° to 135°. In embodiments, the secondary angle depends on the number of (primary, secondary, etc.) sectors/sensing segments of the sensor assembly (and hence the base plate and/or the sensor patch). For example, the secondary angle of the secondary sector can be about 180°±15°, e.g., for a base plate and/or a sensor patch with two or more sectors. The secondary angle of the secondary sector can be about 120°±15°, e.g., for a base plate and/or a sensor patch with two, three, or more sectors. The secondary angle of the secondary sector can be about 90°±15°, e.g., for a base plate and/or a sensor patch with two, three, four, or more sectors.

In embodiments, the first sector and the second sector are non-overlapping. In embodiments of a sensor assembly comprising two sensing segments, the sum of the primary angle and the secondary angle equals 360° (neglecting here a potential reduction of e.g., 10° from the provision of a minor sector allowing sensors to extend into a monitor interface for coupling with a monitor device).

In embodiments, a sensor comprises at least one electrode, such as two electrodes. In embodiments, the sensor assembly comprises an electrode assembly and a support layer. In embodiments, the electrode assembly is arranged, e.g., printed, on the support layer to form the sensor assembly. In embodiments, the sensors (electrodes) of the sensor assembly are configured to detect presence of liquid, such as output from an ostomy, on a proximal surface of the first adhesive layer and/or moisture content in the first adhesive layer. In embodiments, the sensors (electrodes) are configured to detect presence of conductive material, such as liquid and/or solid output from an ostomy, on the proximal surface of the first adhesive layer.

In embodiments, the electrode assembly of the sensor assembly comprises a plurality of electrodes, such as a first electrode, a second electrode, and optionally a third electrode or more electrodes. In embodiments, the plurality of electrodes is configured to detect presence (arranged to facilitate detection) of liquid on the proximal surface of the first adhesive layer and/or moisture content in the first adhesive layer. In embodiments, the electrode assembly of the sensor assembly is configured to detect presence of liquid on the proximal side of the first adhesive layer and/or moisture content in the first adhesive layer in a primary sector and a secondary sector.

Determination of where a leakage/liquid is present/occurring, i.e., moisture pattern types or angular leakage patterns, is useful in helping to reduce the risk of a user experiencing leakage from an ostomy appliance. Further, determination of moisture pattern types and classification of operating states and/or leakage patterns of the ostomy appliance is further useful in helping reduce the risk of skin damage to a user.

In embodiments, the sensor assembly is configured to detect/arranged to facilitate detection of presence of liquid on the proximal surface of the first adhesive layer and/or moisture content in the first adhesive layer in a tertiary sector by means of a tertiary sensing segment. In embodiments, the shape of the tertiary sensing segment resembles an arc of a circle. In embodiments, the tertiary sensing segment defines a tertiary sector of the sensor assembly. In embodiments, the tertiary sensing segment is arranged between two radii. In embodiments, the tertiary sector is arranged in a tertiary angle space from the centre point of the first adhesive layer. In embodiments, the tertiary sector spans a tertiary angle in the range from 45° to 315°, such as in the range from 45° to 180°, for example in the range from 45° to 135°. In embodiments, the tertiary angle depends on the number of (primary, secondary, tertiary, etc.) sectors/sensing segments of the sensor assembly (and hence of the base plate and/or the sensor patch). For example, the tertiary angle of the primary sector can be about 180°±15°, e.g., for a base plate and/or a sensor patch with three or more sectors. The tertiary angle of the tertiary sector can be about 120°±15°, e.g., for a base plate and/or a sensor patch with three or more sectors. The tertiary angle of the tertiary sector can be about 90°±15°, e.g., for a base plate and/or a sensor patch with three, four, or more sectors.

In embodiments, the primary sector and the secondary sector are separate sectors, i.e., non-overlapping. In embodiments, the primary sector and the tertiary sector are separate sectors, i.e., non-overlapping. In embodiments, the secondary sector and the tertiary sector are separate sectors, i.e., non-overlapping.

In embodiments, the primary sector, the secondary sector, and/or the tertiary sector cover electrodes of the sensor assembly embedded (e.g., in combination with a polymeric layer) in the first adhesive layer as well as electrodes of the sensor assembly being exposed to the surroundings. Thereby, the propagation or absorption of moisture in the first adhesive layer can be detected in one or more of the sensing zones by means of the embedded electrodes, thereby providing for the determination of the direction of moisture propagation in the first adhesive layer. Likewise, liquid propagating in the interface between the first adhesive layer and the skin surface can be determined by the exposed electrodes. The electrodes can be exposed by means of sensor point openings. In embodiments, a sensor point opening of the first adhesive layer is configured to overlap with a (sensing) part of an electrode of a sensor, e.g., to form a sensor point. In embodiments, a sensor point opening of the first adhesive layer has a suitable shape and size facilitating access to an electrode of a sensor from the proximal side of the first adhesive layer.

In embodiments, the sensor assembly of the ostomy system comprises one or more electrodes, such as a plurality of electrodes, such as two, three, four, five, six, seven or more electrodes. In embodiments, two electrodes form a sensor. In embodiments, one electrode of a sensor is a ground electrode and a second electrode of a sensor is a sensing electrode. In embodiments, the sensor assembly comprises an electrode assembly comprising the electrode(s) constituting the sensor(s). In embodiments, the electrode assembly is provided in the sensor assembly.

In embodiments, the electrodes, e.g., some or all the electrodes, are arranged between the first adhesive layer and the second adhesive layer. In embodiments, the sensor assembly is arranged between the first adhesive layer and the second adhesive layer. In embodiments, the sensor assembly is arranged on a distal surface of the first adhesive layer. In embodiments, the sensor assembly is arranged on a proximal surface of the first adhesive layer. In embodiments, the sensor assembly comprises an electrode assembly comprising the electrodes making up a/the sensor(s). In embodiments, an electrode comprises a connection part for connecting the electrodes to other components and/or interface terminals/terminal elements, such as for connecting the electrodes to a monitor device. In embodiments, an electrode comprises one or more conductor parts and/or one or more sensing parts. A conductor part can be considered part of an electrode connecting two or more sensing parts, and/or connecting a sensing part with a connection part of the respective electrode. A sensing part can be considered a part of the electrode being suitable for sensing, e.g., liquid, such as liquid content, and/or output. The sensing part can be suitable for sensing e.g., by its shape, said shape potentially being circular, oval, or rectangular. Thus, the conductor part can conduct a signal arising from the sensing part. In embodiments, an electrode comprises alternating conductor parts and sensing parts. In embodiments, the electrode assembly is arranged between the first adhesive layer and the second adhesive layer. The sensor assembly, e.g., an electrode assembly thereof, of the ostomy system, e.g., a base plate and/or a sensor patch incorporating the ostomy system, can comprise a first electrode, a second electrode and optionally a third electrode. The sensor assembly, e.g., an electrode assembly thereof, of the ostomy system, e.g., a base plate and/or a sensor patch incorporating the ostomy system, can comprise a fourth electrode and/or a fifth electrode. Optionally, the sensor assembly, e.g., an electrode assembly thereof, of the ostomy system, e.g., a base plate and/or a sensor patch incorporating the ostomy system, comprises a sixth electrode. In embodiments, the sensor assembly, e.g., an electrode assembly thereof, of the ostomy system, e.g., a base plate and/or a sensor patch incorporating the ostomy system, comprises a ground electrode. The ground electrode can comprise a first electrode part. In embodiments, the first electrode part of the ground electrode forms a ground or reference for the first electrode. In embodiments, the first electrode part forms a closed loop. The ground electrode can comprise a second electrode part. In embodiments, the second electrode part of the ground electrode forms a ground or reference for the second electrode. The ground electrode can comprise a third electrode part. In embodiments, the third electrode part of the ground electrode forms a ground or reference for the third electrode. The ground electrode can comprise a fourth electrode part. In embodiments, the fourth electrode part of the ground electrode forms a ground or reference for the fourth electrode and/or the fifth electrode. In embodiments, the ground electrode is configured as or forms a (common) reference electrode for some or all of the other electrodes of the electrode assembly. Thus, a sensor can be formed between a ground electrode and a (first, second, third, etc.) electrode, such that the sensor comprises the ground electrode and the (first, second, third, etc.) electrode. A potential difference can be applied across the sensor, i.e., across the ground electrode and the (first, second, third, etc.) electrode, by means of a monitor device or a power source. By monitoring the resistance across/between the two electrodes of the sensor, changes in resistance can be attributed changing conditions of the surroundings, such as increasing/decreasing moisture content in the first adhesive layer and/or presence of liquid forming a liquid path (e.g., by connecting two sensor point openings), and hence a short-circuit, between the two electrodes. Thereby is realized a sensor configured to detect/arranged to facilitate detection of liquid on the proximal surface of the first adhesive layer and hence provide a warning to the user that a leakage is imminent.

The electrodes are electrically conductive and can comprise one or more of metallic (e.g., silver, copper, gold, titanium, aluminium, stainless steel), ceramic (e.g., ITO), polymeric (e.g., PEDOT, PANI, PPy), and carbonaceous (e.g., carbon black, carbon nanotube, carbon fibre, graphene, graphite) materials.

In embodiments, the sensor assembly comprises a support layer (also denoted a support film) supporting the electrode assembly. In embodiments, the sensor assembly comprises the electrode assembly and the support layer. One or more electrodes can be formed, e.g., printed, on the proximal side of the support layer. One or more electrodes can be formed, e.g., printed, on the distal side of the support layer. Thus, one or more electrodes can be arranged between the support layer and the first adhesive layer. The sensor assembly and/or the electrode assembly, such as the support layer of the electrode assembly, can have a stomal opening, such as a sensor/electrode assembly stomal opening and/or a support layer stomal opening, with a centre point. In embodiments, the support layer comprises polymeric (e.g., polyurethane, PTFE, PVDF) and/or ceramic (e.g., alumina, silica) materials. In one or more exemplary base plates and/or sensor patches, the support layer is made of thermoplastic polyurethane (TPU). The support layer material can be made of or comprise one or more of polyester, a thermoplastic elastomer (TPE), polyimide, polyimide, ethylene-vinyl acetate (EVA), polyurea, and silicones. Exemplary thermoplastic elastomers of the support layer are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

In embodiments, two electrodes of the electrode assembly form a sensor. In embodiments, a first electrode and a second electrode form the primary sensing segment for detecting presence of liquid on the proximal side of the first adhesive layer in the primary sector. In embodiments, the second electrode and a third electrode form the secondary sensing segment for detecting presence of liquid on the proximal side of the first adhesive layer in the secondary sector. In embodiments, the first electrode and the third electrode form the tertiary sensing segment for detecting presence of liquid on the proximal side of the first adhesive layer in a tertiary sector. In embodiments, a fourth electrode and a fifth electrode form the second sensor for detecting presence of liquid on the proximal side of the first adhesive layer continuously about the first sensor. In embodiments, one of the first, second, third, fourth, and fifth electrode is a (common) ground electrode in order to reduce complexity of the electrode assembly.

In embodiments, the sensor assembly comprises a monitor interface. In embodiments, the base plate and/or sensor patch incorporating parts of the ostomy system according to the invention comprises a monitor interface. In embodiments, the monitor interface is configured for electrically and/or mechanically connecting the sensor assembly (and/or base plate or sensor patch) to a monitor device. In embodiments, the monitor interface is configured for wirelessly connecting the sensor assembly (and/or base plate or sensor patch) to the monitor device. Thus, the monitor interface of the sensor assembly can be configured to electrically and/or mechanically couple the sensor assembly and the monitor device, such as to couple a base plate and/or sensor patch incorporating the first adhesive layer and the sensor assembly of the ostomy system to the monitor device of the ostomy system. In embodiments, the monitor interface comprises terminals providing electrical connections to the sensors. Thus, the sensors, such as electrodes of the sensors, extend into the monitor interface. In embodiments, the monitor interface is provided in a neck portion of the first adhesive layer, such as in a neck portion of a base plate or a sensor patch. In embodiments, the neck portion is configured to adhere to the skin surface of the user. In embodiments, the neck portion serves to distance the monitor device from the peristomal skin area and/or the sensors provided in the sensor assembly.

In embodiments, the monitor interface of the sensor assembly—or the base plate and/or sensor patch incorporating the sensor assembly—comprises, e.g., as part of a first connector of the monitor interface, a coupling part for forming a mechanical connection, such as a releasable coupling between the monitor device and the sensor assembly. In embodiments, the coupling part is configured to engage with a coupling part of the monitor device for releasably coupling the monitor device to the base plate and/or the sensor patch and hence the sensor assembly.

In embodiments, the monitor device comprises a housing, a processor, a memory, a first interface connected to the processor and the memory, and a second interface connected to the processor. The first interface is configured for obtaining ostomy data from the sensor assembly, e.g., the base plate and/or the sensor patch comprising a sensor assembly and coupled to the first interface. The ostomy data comprises primary ostomy data from a first sensor of the sensor assembly, e.g., of the base plate and/or the sensor patch comprising a sensor assembly, and secondary ostomy data from a second sensor of the sensor assembly, e.g., of the base plate and/or the sensor patch comprising a sensor assembly. In embodiments, the processor is configured to: obtain primary parameter data based on the primary ostomy data; obtain secondary parameter data based on the secondary ostomy data; and detect presence of liquid on the proximal side of the first adhesive layer and/or moisture in the first adhesive layer in a primary sensing zone based on the primary parameter data. In embodiments, the primary sensing zone is arranged in a primary sector of the sensor assembly, or of the first adhesive layer comprising a sensor assembly as disclosed. Further, in embodiments, the processor is configured to detect presence of liquid on the proximal side of the first adhesive layer and/or moisture in the first adhesive layer in a secondary sensing zone based on the secondary parameter data. In embodiments, the secondary sensing zone is arranged in a secondary sector of the sensor assembly, or of the first adhesive layer comprising a sensor assembly as disclosed. In embodiments, in accordance with a detection of presence of liquid and/or moisture in the primary sensing zone, the processor is configured to transmit a primary monitor signal comprising monitor data indicative of presence of liquid and/or moisture in the primary sensing zone via the second interface; and in accordance with a detection of presence of liquid and/or moisture in the secondary sensing zone, transmit a secondary monitor signal comprising monitor data indicative of presence of liquid and/or moisture in the secondary sensing zone via the second interface.

Providing a base plate having sensing capabilities, e.g., through an incorporated sensor assembly or through a sensor patch comprising a sensor assembly, provides for an optimum or improved use of an ostomy appliance. In particular, it is facilitated that a base plate is not changed too late (leading to adhesive failure, leakage and/or skin damage), or at least that a user is informed that a leakage will happen, is happening, or has happened. Accordingly, the user or a health care professional is able to monitor and plan the use of the ostomy appliance.

The monitor device is configured to detect liquid at the primary sensing segment and/or at the secondary sensing segment of the first sensor, and to detect liquid at the second sensor. For example, the monitor device can be configured to detect liquid by means of applying a potential difference/voltage across an electrode pair forming a respective sensor and to monitor changes in resistance across the electrode pair, where changes in resistance are indicative of changes in moisture content in the first adhesive layer and/or presence of liquid at the respective electrode pair (sensor). In embodiments, liquid at the primary sensing segment, the secondary sensing segment, and/or the second sensor can be detected by providing the first adhesive layer with a series of sensor point openings exposing the electrodes of the respective sensing segments/sensors to the interface between the skin surface and the proximal surface of the first adhesive layer. Thereby, liquid present in the interface is likely to enter the sensor point openings and create a liquid path between two (e.g., adjacent) sensor point opening and thereby short-circuit the electrodes forming the respective sensor and thereby provide a signal indicative of presence of liquid at the respective sensor.

The monitor device is further configured to determine a main sector of the sensor assembly, the main sector comprising the primary and/or secondary sector wherein liquid has been detected by the primary and/or secondary sensing segment, respectively. In embodiments, the main sector is the primary sector. For example, the main sector is the primary sector if liquid has been detected at the primary sensing segment and not at other (e.g., the secondary) sensing segments. In embodiments, the main sector is the secondary sector if liquid has been detected at the secondary sensing segment and not at other (e.g., the primary) sensing segments. In embodiments, the main sector comprises the primary sector and the secondary sector if liquid has been detected at both the primary sensing segment and the secondary sensing segment. In embodiments comprising three or more sensing segments (e.g., a tertiary sensing segment and hence a tertiary sector), the main sector can be the tertiary sector if liquid has been detected at the tertiary sensing segment and not at other (e.g., the primary and the secondary) sensing segments, and so forth. Thus, the main sector is conditional on the detection of liquid in at least one sector of the sensor assembly. In embodiments, the main sector is determined upon detection of liquid at the first sensor. In embodiments, the main sector is determined upon detection of liquid at both the first sensor and the second sensor. In embodiments, the monitor device is configured to determine the main sector once liquid has been detected at the first sensor (i.e., at the primary sensing segment and/or the secondary sensing segment). In embodiments, the monitor device is configured to determine the main sector once liquid has been detected both at the first sensor and at the second sensor. The main sector can be considered a volatile sector. By volatile is meant that the main sector is a sector determined by the monitor device and can change if conditions change (e.g., if liquid is detected at further/additional sensing segments of the first sensor following detection at one (e.g., the primary) sensing segment). Thus, the main sector is conditional on a detection of liquid at the first sensor, e.g., at the primary sensing segment and/or at the secondary sensing segment. Thus, the main sector comprises the sectors of the sensor assembly where liquid has been detected.

The monitor device is configured to indicate a site of leakage from the ostomy appliance based on at least the main sector. By a site of leakage is meant the site/location/position about the periphery of the base plate of the ostomy appliance where leakage is (most likely) about to occur. By indicating is meant that the monitor device is configured to suggest the site of leakage, i.e., in advance of the actual leakage. In other words, by indicate is meant that the monitor device is capable of pointing out/predicting the site of leakage in advance of the actual leakage, based on specific historic data, namely at least the main sector. Thus, by utilizing historic data—e.g., as contained in the main sector, since the main sector is determined based on past detections of liquid at sensors—the monitor device is capable of indicating the site of leakage to be within the main sector. In embodiments, an accuracy can be assigned to the site of leakage due to the indication being the result of past events (detection of liquid at the first sensor and/or the second sensor) and/or when basing the site on leakage on both the main sector and a time-delay, as will be described below. By indicating such site of leakage in advance of the actual leakage, the user is provided with the opportunity to take remedying actions, e.g., by changing his/her ostomy appliance (base plate). In embodiments, indicating a site of leakage is equivalent to predicting a site of leakage. In embodiments, indicating comprises determining, estimating, and/or calculating.

In embodiments, by indicating a site of leakage is meant to transmit a signal from the monitor device to an accessory device and to visualize the site of leakage on a user interface of said accessory device. In embodiments, by indicating a site of leakage is meant to transmit information pertaining to/indicative of a determined site of leakage to an accessory device and optionally to visualize the information in a (graphical) user interface thereof. Thus, by the monitor device indicating the site of leakage does not necessarily comprise the monitor device visualizing the site of leakage.

In embodiments, the site of leakage as indicated by the monitor device is within the main sector, i.e., within the sector(s) where liquid was detected by the sensing segments of the first sensor.

In embodiments, indicating the site of leakage comprises indicating the main sector of the first adhesive layer in a graphical representation of said first adhesive layer or the peristomal skin area. In embodiments, the graphical representation is provided in a graphical user interface of an accessory device, such as in an app of a smartphone/watch.

Several factors affect why the site of leakage is likely to be within the main sector (the sector(s) wherein liquid has been detected by the first sensor). One factor to consider is the gradual detachment of the first adhesive layer of the ostomy system due to presence of liquid in the interface between the first adhesive layer and the skin surface. Once liquid, in particular output emanating from the stoma, enters the interface by the stomal opening, the adhesive can start to degrade and ultimately detach from the skin. Such detachment causes an acute angle to form between the attached adhesive and the detached adhesive. The acute angle eases further detachment of the adhesive due to the output finding the path of least resistance and possibly due to a continued amount of output entering the interface. The further detachment eventually causes leakage to be at the indicated site of leakage, the indicated site of leakage being at a point along the part of the periphery of the first adhesive layer residing within the main sector. Thus, when liquid (output) has been detected by the first sensor within a certain sector, the gradual detachment of the adhesive is most likely to propagate within the same sector due to the propagating output finding the path of least resistance initially created by the detached adhesive.

The sensor assembly as disclosed above comprises a relatively simple layout of sensors, since only the first sensor is provided with means (sensing segments) for determining a direction of liquid, whereas the second sensor is a continuous sensor encircling the (entire) first sensor. Surprisingly, the inventors have found that by providing the sensor assembly as part of an ostomy system further comprising a monitor device, it is possible to indicate a site of leakage based on a statistical analysis—such as by taking into account the main sector based on historic data. In other words, it has been found that the complexity of the sensor assembly, e.g., in terms of manufacturing, is reduced without greatly compromising the accuracy of the system in terms of its ability to indicate a site of leakage. Thus, the ostomy system as disclosed provides a simple sensor assembly with the ability to indicate a site of leakage based on (past) readings of the sensors/sensing segments. Thus, by utilizing detections of leakage at the first sensor and the second sensor, the ostomy system, by means of the monitor device, is capable of indicating a site of leakage. In other words, the complexity of the sensor assembly can be reduced without greatly compromising the given sensing sensitivity of the ostomy system.

In embodiments, an accessory device is configured to perform some or all of the described tasks of the monitor device. In embodiments, the monitor device transmits/relays unprocessed data to an accessory device.

In an embodiment, the monitor device is further configured to determine a time delay between detecting liquid at the first sensor and detecting liquid at the second sensor. Thus, the monitor device configured to determine a (first) time difference between detecting liquid at a sensing segment of the first sensor and at the second sensor.

The first sensor comprising the primary and secondary sensing segments—and optionally additional sensing segments—is arranged closer to the centre point/stomal opening than the second sensor when seen in a radial direction from the centre point; the second sensor encloses the first sensor. Since output emanates from the stoma, it will likely reach the first sensor before reaching the second sensor—in cases where the output has entered the interface between the skin surface and the first adhesive layer of the ostomy system as disclosed. Thus, in embodiments, upon detection of liquid at the first sensor, e.g., the primary sensing segment and/or the secondary sensing segment, a first time stamp is included in the primary ostomy data pertaining to the detection of liquid at the first sensor, and upon detection of liquid at the second sensor, a second time stamp is included in the secondary ostomy data pertaining to the detection of liquid at the second sensor. By comparing the primary and secondary ostomy data, the time delay/difference between when liquid was detected at the first sensor and when liquid was detected at the second sensor can be calculated. In embodiments, the time delay is a parameter affecting the indication of a site of leakage, such as the accuracy of the indication.

In embodiments, by considering the time delay, output can be differentiated from sweat, since the latter is more likely to generate signals irrespective of the stoma, whereas output is more likely to cause a detection at the first sensor (closest to the stoma) prior to a detection at the second sensor (further away from the stoma than the first sensor). In embodiments, a positive time delay (the first sensor detects liquid prior to the second sensor) indicates propagation of output in the interface. In embodiments, a negative time delay (the second sensor detects liquid prior to the first sensor) is indicative of sweat in the interface. In embodiments, the monitor device is configured to generate a notification if the time delay is negative, the notification alerting the user of the presence of sweat in the interface. The presence of sweat can accelerate liquid propagation and/or reduce the wear time of the base plate, and thus can be beneficial to be notified about.

In embodiments, an accessory device is configured to determine a time delay between detecting liquid at the primary and/or secondary sensing segment and detecting liquid at the second sensor.

In an embodiment, the monitor device is configured to indicate the site of leakage based on at least the main sector and the time delay.

In embodiments, indicating the site of leakage comprises indicating the main sector of the first adhesive layer and an associated accuracy that the leakage is indeed about to happen here. For example, the associated accuracy of the indication is provided in a user interface, such as in a graphical user interface of an accessory device, such as in an app of a smartphone/watch. In embodiments, the accuracy is provided as a numerical value. In embodiments, the accuracy is provided as a statement selected from a plurality of statements pertaining to the accuracy of the indicated site of leakage. In embodiments, the accuracy is visualized as a colour selected from a colour code included in a graphical representation of the site of leakage, e.g., as a colour of a graphical representation of the main sector. In embodiments, the accuracy is a probability. In embodiments, the accuracy/probability is determined by means of the monitor device. In embodiments, the accuracy is based on the time delay. In embodiments, the accuracy is based on historic use of an ostomy system according to the invention.

As disclosed above, by indicating is meant pointing out the most probable site of leakage, since the site of leakage pertains to a future event (the actual leakage) and the indication is based on past events (detecting liquid at various locations in the interface between the skin surface and the first adhesive layer). Thus, an accuracy can be associated with the indicated site of leakage since conditions may change before an actual leakage (in the event that the user does not react to an issued notification alerting him/her of the imminent leakage).

In embodiments, one parameter affecting the indicated site of leakage—in particular the accuracy of the indicated site of leakage—is the time delay. Fast propagating output—e.g., due to the poor initial adhesion, wrinkles, or a large amount of output bypassing the ostomy appliance—can pass through the interface and become leakage in a matter of minutes, whereas slowly propagating output can take several hours to pass through the interface. A fast propagating output will provide a short time delay between detections of liquid at the first sensor and the second sensor, respectively. On the contrary, the slowly propagating output will provide a large time delay.

During the short time delay of quickly propagating output, the probability of the output being within the determined main sector (determined based on reading from the first sensor) upon reaching the second sensor is relatively large. In other words, the probability that the output spreads to neighbouring sectors in the time between being detected at the first sensor and the second sensor is relatively low. On the contrary, during the large time delay of slowly propagating output, the probability of the output being within the determined main sector (determined based on readings from the first sensor) upon reaching the second sensor is relatively small. In other words, the probability that the output spreads to neighbouring sectors between being detected at the first sensor and the second sensor is relatively high.

Thus, based on the time delay, the monitor device is configured to indicate the site of leakage. In embodiments, indicating the site of leakage includes visually depicting the main sector and an accuracy associated with the main sector—where the time delay was large, the associated accuracy will be low, and where the time delay was short, the associated accuracy will be high.

In embodiments, if the time delay is less than 60 minutes, the associated accuracy of the site of leakage is considered high, and thus, the monitor device and/or accessory device is configured to generate a numerical value, statement, and/or colour representing such accuracy. In embodiments, the associated accuracy of the site of leakage is considered high if the time delay is less than 60, such as less than 45 minutes, such as less than 30 minutes, such as less than 25 minutes, such as less than 20 minutes, such as less than 15 minutes, such as less than 10 minutes, such as less than 8 minutes, such as less than 5 minutes, such as less than 4 minutes, such as less than 3 minutes, such as less than 2 minutes, such as less than 1 minute.

In embodiments, if the time delay is greater than 60 minutes, the associated accuracy of the site of leakage is considered low, and thus, the monitor device and/or accessory device is configured to generate a numerical value, statement, and/or colour representing such accuracy. In embodiments, the associated accuracy of the site of leakage is considered low if the time delay is greater than 60 minutes, such as greater than 45 minutes, such as greater than 30 minutes, such as greater than 25 minutes, such as greater than 20 minutes, such as greater than 15 minutes, such as greater than 10 minutes, such as greater than 8 minutes, such as greater than 5 minutes, such as greater than 4 minutes, such as greater than 3 minutes, such as greater than 2 minutes, such as greater than 1 minute.

In embodiments, an accessory device is configured to indicate the site of leakage based on at least the main sector and the time delay.

In an embodiment, the monitor device is configured to indicate a remaining wear time of the first adhesive layer based on the main sector and/or the time delay. For example, where the first adhesive layer of the ostomy appliance is provided/incorporated in a base plate or a sensor patch, the monitor device is configured to indicate a remaining wear time of such base plate and/or sensor patch. By remaining wear time is meant time before leakage from the base plate. In embodiments, the remaining wear time is an estimate. By knowing the remaining wear time, or an estimate of the remaining wear time, the user is provided with a time frame allowing him/her to take remedying actions, such as identifying a restroom location and/or changing his/her base plate, before leakage occurs.

In embodiments, the remaining wear time is based on the main sector. For example, the remaining wear time can be affected by the location of the main sector about the user's stoma. For example, if the main sector (thus, the output) is arranged in/near wrinkles/folds in the skin, the remaining wear time can be short. Thus, the monitor device is configured to indicate the remaining wear time based on the main sector, such as based on the location of the main sector relative to certain anatomic features (wrinkles, folds, scar tissue, etc.) in the peristomal skin area.

In embodiments, the remaining wear time is based on the time delay. The time delay reflects the time difference between liquid was detected at the first sensor and at the second sensor. In embodiments, by knowing the (radial) distance from the second sensor to the periphery of the base plate and by extrapolating the time delay, the remaining wear time can be estimated and indicated. Thus, a large time delay can indicate a large remaining wear time, whereas a short time delay can indicate a short remaining wear time.

In embodiments, an accessory device is configured to indicate the remaining wear time.

In an embodiment, a sensor and/or sensing segment comprises a ground electrode and a sensing electrode, and the monitor device is configured to detect a short-circuit between the ground electrode and the sensing electrode. A short-circuit can be indicative of liquid at the respective sensor and/or sensing segment.

As previously disclosed, in embodiments, two electrodes form a sensor, and the monitor device can be configured to sense/monitor a resistance across the two electrodes, such as to determine an adhesive performance of the first adhesive layer and/or to detect a short-circuit. In embodiments, the short-circuit is facilitated by the provision of two or more sensor point openings exposing the sensors/sensing segments to the surroundings, including the proximal surface of the first adhesive layer. Thus, the sensor point openings provide for liquid to form a liquid/conductive path between the two electrodes of the sensor and thereby provide for a signal indicating presence of liquid at the respective sensor/sensing segment.

In an embodiment, the first sensor further comprises a tertiary sensing segment arranged in a tertiary sector of the sensor assembly.

In an embodiment, the primary, secondary, and tertiary sector are non-coinciding and each span an angle of 120 degrees.

In an embodiment, the monitor device is further configured to detect liquid at the tertiary sensing segment of the first sensor.

As previously disclosed, in embodiments, the first sensor is divided into three or more sensing segments, such as to provide a higher sensing sensitivity. In embodiments, the primary, secondary, and tertiary sensing segment define a primary, secondary, and tertiary sector, respectively, each having/spanning a central angle of 120°, such that said sensing segments provide means for detecting liquid in sectors of equal size/angle. The sectors are non-coinciding/non-overlapping when seen in the radial direction, such that detections of liquid at one sensing segment is associated with a single sector only.

The monitor device is configured to apply the same functionalities as previously disclosed in relation to the primary and secondary sensing segment/sector to the tertiary sensing segment/sector. Thus, the monitor device is configured to detect liquid at the tertiary sensing segment, and upon detection of liquid at the tertiary sensing segment to include the tertiary sensing segment in the main sector.

In embodiments, the same reasoning applies to N sensing segments, where each sensing segment defines a sector having a central angle of 360°/N, and where the monitor device is configured to apply the same functionalities to the N sensing segments as previously disclosed in relation to the primary, secondary, and tertiary sensing segments.

In an embodiment, the sensor assembly comprises a third sensor arranged between the first sensor and the second sensor. In embodiments, the third sensor encloses, such as is concentrical about, the first sensor. In embodiments, the third sensor comprises at least two sensing segments. In embodiments, the third sensor is continuous about the first sensor.

Providing a third sensor as disclosed provides for an increased coverage of the peristomal skin area and thus increases the sensing sensitivity in a radial direction. Thereby, propagation of liquid in the interface can be detected to a greater detail. Thereby, an estimation of the remaining wear time can be improved since the speed of the propagating liquid can be determined to a greater detail and/or dynamics of the liquid in the interface can be monitored to a greater detail.

In embodiments, the third sensor is divided into sensing segments, i.e., similar to the first sensor. In embodiments, the third sensor comprises the same number of sensing segments as the first sensor. In embodiments, sensing segments of the third sensor are aligned with sensing segments of the first sensor, such that a primary sensing segment of the third sensor is arranged within the primary sector as defined by the primary sensing segment of the first sensor, etc. In embodiments, the sensing segments of the third sensor are rotated by an angle relative to the sensing segments of the first sensor. For example, the primary sensing segment of the third sensor is rotated by half the primary angle of the first sensor. Thereby, the number of sectors of the sensor assembly is doubled.

In embodiments, the third sensor is continuous about the first sensor, i.e. similar to the second sensor. Thereby, the third sensor essentially comprises the same functionalities and features as the second sensor as disclosed previously.

In an embodiment, the monitor device is further configured to indicate a propagation of liquid based on one or more additional detections of liquid at a sensing segment of the first sensor.

Following a detection of liquid at a sensing segment of the first sensor, the liquid can propagate and cause a detection at another sensing segment of the first sensor. For example, where liquid was initially detected at the primary sensing segment, detection of liquid at the secondary sensing segment indicates a propagation into the second sector. Likewise, in embodiments wherein the first sensor comprises three or more sensing segments, the propagation can be from one of the three or more sensing segments and into another of the three or more sensing segments. In embodiments, propagation/detection of liquid at an additional sensing segment may be detected before liquid is detected at the second sensor. In embodiments, propagation/detection of liquid at an additional sensing segment may be detected after liquid is detected at the second sensor. In embodiments, the monitor device is configured to indicate where and when the propagation occurs, i.e., into which sectors and whether the propagation is before or after detection of liquid at the second sensor.

In embodiments, by indicating a propagation of liquid is meant to transmit information pertaining to the propagation of liquid to an accessory device and optionally to visualize the information in a (graphical) user interface thereof.

In an embodiment, the monitor device is configured to determine and assign an accuracy to the indicated site of leakage and/or the propagation of liquid. As previously discussed, an accuracy can be determined based on the detections of liquid at the first and/or second sensor, and such accuracy can be assigned the indicated site of leakage. In embodiments, the monitor device is further configured to determine and assign an accuracy to the propagation of liquid. In embodiments, the monitor device is configured to determine a time delay between detecting liquid at one, e.g., the primary, sensing segment of the first sensor, and detecting liquid at a second, e.g., the secondary, sensing segment of the first sensor. In embodiments, determining an accuracy of the indicated propagation of liquid is based on such time delay.

In a second aspect of the invention, a sensor assembly for an ostomy appliance of an ostomy system is disclosed. The sensor assembly is configured for attachment to a first adhesive layer of the ostomy appliance. The sensor assembly comprises a first sensor configured to at least partly encircle a centre point of the first adhesive layer and a second sensor at least partly encircling the first sensor. The first sensor and the second sensor are adapted to facilitate detection of liquid on a proximal surface of the first adhesive layer. The first sensor comprises at least a primary sensing segment arranged in a primary sector of the sensor assembly and a secondary sensing segment arranged in a secondary sector of the sensor assembly.

The sensor assembly of the second aspect of the invention is configured to be embedded/incorporated in an ostomy appliance of an ostomy system according to the first aspect of the invention. Hence, the features and advantages as disclosed in relation of the sensor assembly of the ostomy appliance of the first aspect of the invention are applicable to the sensor assembly according to the second aspect of the invention. In embodiments, the sensor assembly is configured for attachment to a first adhesive layer of a base plate. In embodiments, the sensor assembly is configured for attachment to a first adhesive layer of a sensor patch for a base plate.

In embodiments, the sensor assembly of the second aspect of the invention comprises an electrode assembly and a support layer. In embodiments, the electrode assembly comprises one or more electrodes. In embodiments, a sensor of the sensor assembly comprises the one or more electrodes of the electrode assembly. In embodiments, the first sensor and the second sensor are arranged on a support layer. In embodiments, the electrodes of the electrode assembly are provided/arranged on a surface of the support layer, such as a proximal surface of the support layer. In embodiments, the electrodes of the electrode assembly are printed on a surface of the support layer. In embodiments, the sensor assembly is configured for attachment to a proximal surface of the first adhesive layer. In embodiments, the sensor assembly is configured for attachment to a distal surface of the first adhesive layer. In embodiments, the sensor assembly is attached a first adhesive layer, such as a distal surface of a first adhesive layer. In embodiments, the sensor assembly is attachable to a first adhesive layer of an ostomy appliance, such as a first adhesive layer of a base plate or a sensor patch for attachment to a base plate. In embodiments, the sensor assembly provides a generic base plate with an ability to sense liquid, such as output, and/or moisture content in the first adhesive layer.

In an embodiment, the first sensor of the sensor assembly further comprises a tertiary sensing segment arranged in a tertiary sector of the sensor assembly. A tertiary sensing segment arranged in/defining a tertiary sector of the sensor assembly provides the functionalities as previously disclosed in relation to the sensor assembly of the ostomy system according to the first aspect of the invention.

In a third aspect of the invention, a method, performed in a monitor device, for predicting a site of leakage from an ostomy appliance of an ostomy system according to the first aspect of the invention is disclosed. The method comprises the steps of detecting liquid at the primary sensing segment and/or the secondary sensing segment of the first sensor, detecting liquid at the second sensor, determining a main sector of the sensor assembly comprising the primary and/or secondary sector wherein liquid has been detected by the primary and/or secondary sensing segment, respectively, and indicating a site of leakage from the ostomy appliance, the site of leakage being based on at least the main sector.

Definitions, embodiments, features, and/or functionalities discussed in relation to the ostomy system and/or the sensor assembly according to the first and/or second aspect of the invention are likewise applicable to the method.

The ostomy system comprises a monitor device and an ostomy appliance having a first adhesive layer and a sensor assembly. Features and functionalities of the ostomy system as disclosed in relation to the first aspect of the invention disclosed above are considered applicable to the method as disclosed herein. In embodiments, the method is performed in the monitor device. In embodiments, the method is performed in a monitor device in communication with an accessory device. References to features in the method are references to features in the ostomy system and/or sensor assembly disclosed above.

In embodiments, by indicating a site of leakage is meant to transmit a signal from the monitor device to an accessory device and to indicate the site of leakage on a user interface of said accessory device. In embodiments, by indicating a site of leakage is meant to transmit information pertaining to a determined site of leakage to an accessory device and optionally to visualize the information in a (graphical) user interface thereof. Thus, indicating the site of leakage does not necessarily comprise visualizing the site of leakage.

In an embodiment, the method further comprises the step of determining a time delay between detecting liquid at the first sensor and detecting liquid at the second sensor.

As previously disclosed, the second sensor encircles/encloses (the sensing segments of) the first sensor. Thus, the time delay can be calculated by associating a time stamp to the detection of liquid at a sensor and by subtracting the time stamps. In other words, in embodiments, upon detection of liquid at the first sensor, e.g., the primary sensing segment and/or the secondary sensing segment, a first timestamp is included in primary ostomy data pertaining to the detection of liquid at the first sensor, and upon detection of liquid at the second sensor, a second time stamp is included in the secondary ostomy data pertaining to the detection of liquid at the second data. By comparing the primary and secondary ostomy data, the time delay/difference between when liquid was detected at the first sensor and when liquid was detected at the second sensor can be calculated. In embodiments, the time delay is a parameter affecting the indication of a site of leakage, such as the accuracy of the indication.

In embodiments, a positive time delay (the first sensor detects liquid prior to the second sensor) indicates presence/propagation of output in the interface. In embodiments, a negative time delay (the second sensor detects liquid prior to the first sensor) indicates sweat in the interface.

In an embodiment, the site of leakage is being based on at least the main sector and the time delay.

Thus, the method comprises considering the main sector and the time delay when indicating the site of leakage. In other words, the method comprises indicating the site of leakage from the ostomy appliance, the site of leakage being based on the main sector and the time delay.

In an embodiment, the method comprises indicating a propagation of liquid based on one or more additional detections of liquid at a sensing segment of the first sensor.

In embodiments, the method comprises the additional steps of detecting liquid at further sensing segments of the first sensor and indicating a propagation of liquid based on such detections at further sensing segments of the first sensor. In embodiments, by propagation is meant the spreading of liquid into additional, such as neighbouring, sectors of the sensor assembly. Thus, propagation can indicate a more severe or developing case of liquid in the interface, which may provide certain details to the user or HCP.

DETAILED DESCRIPTION OF THE DRAWINGS

Figure 1B:
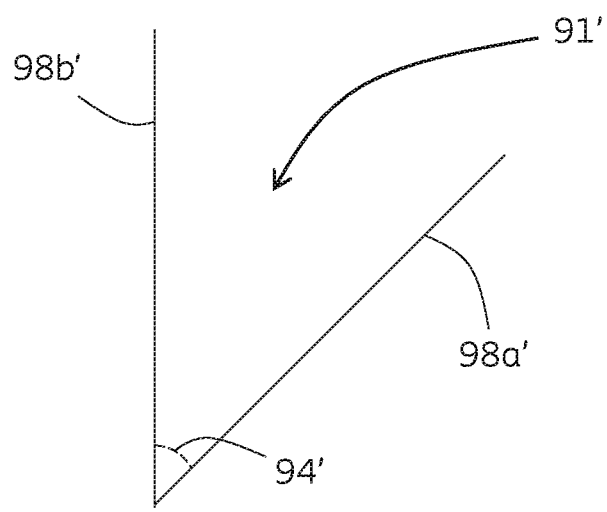
FIG. 1B illustrates a sector of a circle according to Euclidean geometry.

FIG. 1A illustrates a circle 90 according to Euclidean geometry included herein for the purpose of establishing the nomenclature used in the following description. A sector 91 defined by two radii 98a,98b and an arc 93 of the circle 90 is illustrated. The two radii 98a,98b are separated by a central angle 94. As illustrated in FIG. 1B, a sector 91' can be defined through two radii 98a',98b' and a central angle 94' only. References to a sector throughout the present disclosure relates to a sector according to FIG. 1B unless otherwise specified. Thus, a sector as referred to in the present disclosure extends to infinity unless otherwise specified. Thereby, when specifying that an event or feature appear within a certain sector, such event or feature appear in the space/area/region defined/bound by the two (infinite) radii 98a',98b' and the central angle 94'.

In embodiments of the invention, a sector can be delimited by an edge of a first adhesive layer and/or a sensor assembly or a sensor of the sensor assembly. Throughout the disclosure, specific sectors are denoted a primary sector, secondary sector, etc., and the central angle separating the two radii is denoted the primary angle, secondary angle, etc., respectively. Multiple sectors can be arranged adjacent each other. Sectors are non-overlapping.

Figure 2A:
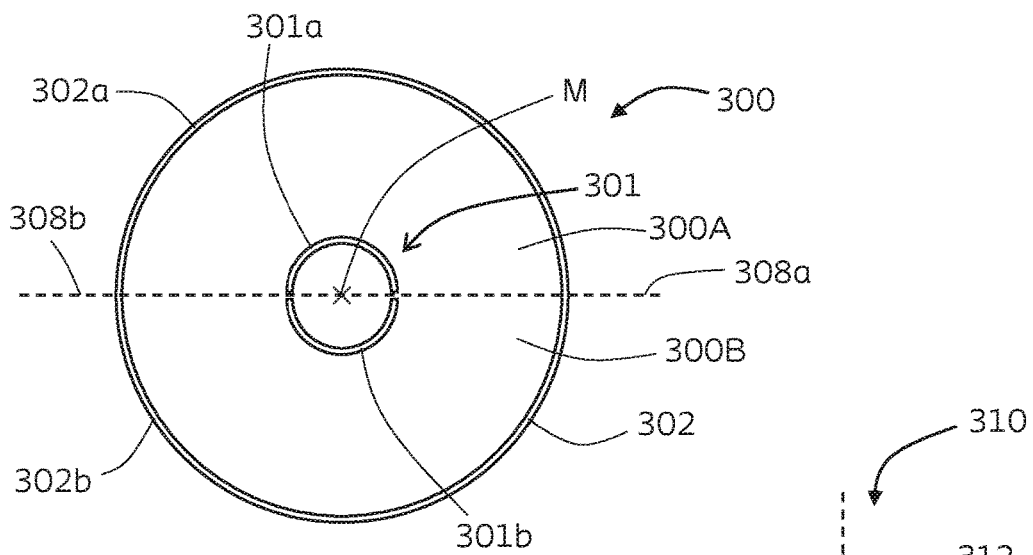
FIG. 2A illustrates an exemplary sensor assembly according to an embodiment of the invention.
Figure 2B:
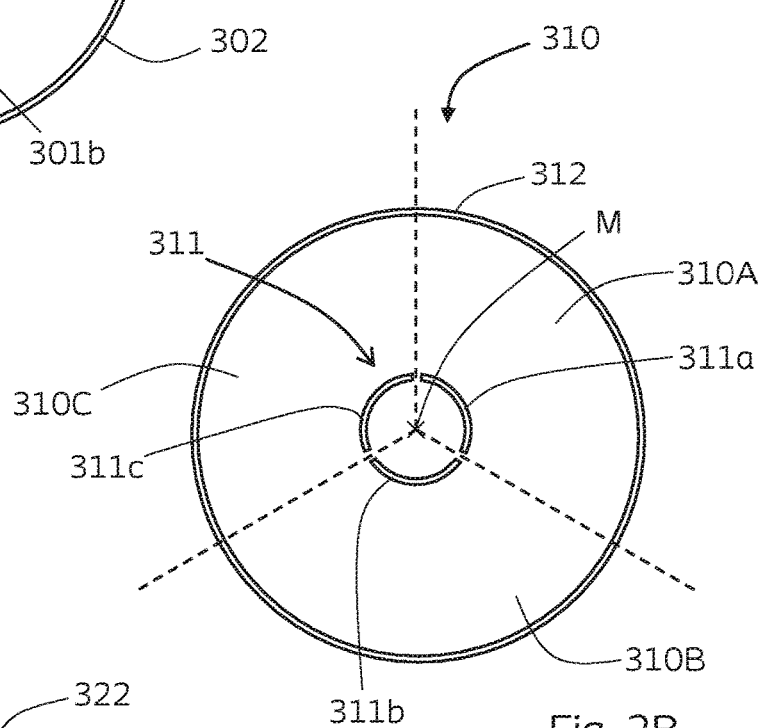
FIG. 2B illustrates an exemplary sensor assembly according to an embodiment of the invention.
Figure 2C:
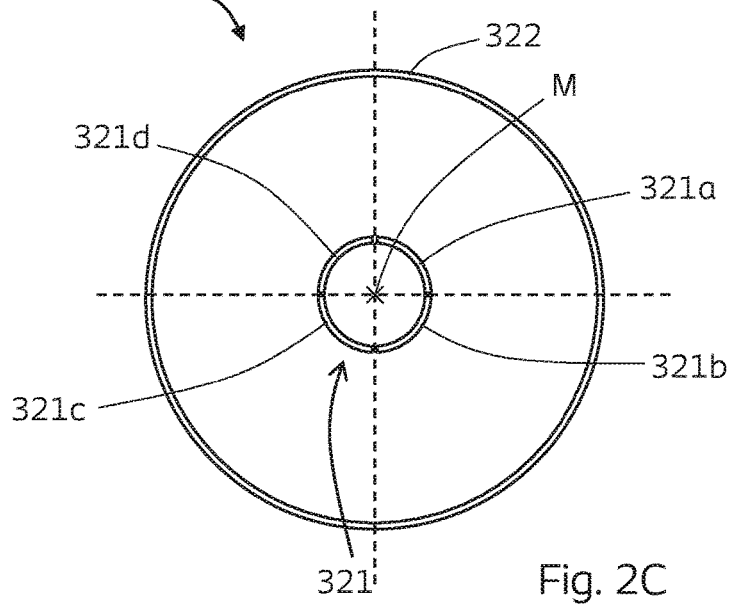
FIG. 2C illustrates an exemplary sensor assembly according to an embodiment of the invention.

FIGS. 2A-2C illustrate exemplary sensor assemblies 300, 310,320 comprising a first sensor and a second sensor according to the invention. The exemplary sensor assemblies highlight the relative arrangement of the sensors but is not necessarily intended to illustrate specific embodiments of the sensors or means for communicating with said sensors. Dashed radial lines (radii) illustrate the division of the sensor assemblies into sectors defined by the extent of the sensing segments of the first sensor 301,311,321, and thus are included to increase the intelligibility only. Thus, particular attention is drawn to the division of the first sensor 301,311,321 into sensing segments, such that the first sensor is essentially circular, but divided into separate segments. This is elaborated further in the following.

In FIG. 2A, the first sensor 301 encircles a centre point M of the sensor assembly 300. The centre point M of the sensor assembly 300 is configured to align/coincide with a centre point of a first adhesive layer. Thereby, the sensor assembly 300 is symmetrically arranged about such centre point of a first adhesive layer. The first sensor 300 is divided into two sensing segments, a primary sensing segment 301a and a secondary sensing segment 301b. Each sensing segment 301a,301b defines a sector 300A,300B. The sectors 300A, 300B extend to infinity as described in relation to FIG. 1B. Each sensing segment 301a,301b covers a half circle (180°), and thus, each sector 300A,300B is defined by the radii 308a,308b (dashed horizontal line) and a primary (central) angle and a secondary (central) angle, the primary and secondary angles being equal and 180° each. Each sensing segment 301a,301b is configured to detect presence of liquid independently of the other. Thus, a detection of liquid at the primary sensing segment 301a is indicative of liquid being present in/spreading into the primary sector 300A, and a detection of liquid at the secondary sensing segment 301b is indicative of liquid being present in/spreading into the secondary sector 300B.

The second sensor 302 encircles the first sensor 301. The second sensor 302 is continuous about the first sensor 301. In other words, in embodiments, the second sensor 302 is not divided into sensing segments as discussed in relation to the first sensor 301. Thus, in embodiments, the second sensor 302 is not configured to distinguish detections of liquid in one sector from another. Rather, the second sensor 302 is configured to detect liquid about the first sensor 301 without the ability to distinguish the location of the liquid. Thereby, in embodiments, the second sensor 302 can be considered simpler than the first sensor 301. From the definition of a sector above, a primary part 302a of the second sensor 302 is arranged/resides within the primary sector 300A, and a secondary part 302b of the second sensor 302 is arranged/resides within the secondary sector 300B. Thus, when seen in a radial direction from the centre point M, an overlap exists between the primary sensing segment 301a and the primary part 302a of the second sensor 302 arranged within the primary sector 300A and between the secondary sensing segment 301b and the secondary part 302b of the second sensor 302 arranged within the secondary sector 300B.

FIG. 2B illustrates an exemplary sensor assembly 310 similar to the one illustrated in FIG. 2A. The sensor assembly 310 of FIG. 2B differs from the sensor assembly 300 of FIG. 2A by that the first sensor 311 comprises three sensing segments; a primary sensing segment 311a, a secondary sensing segment 311b, and a tertiary sensing segment 311c. Each of the three sensing segments defines a sector having a central angle of 120°. The primary sensing segment 311a defines a primary sector 310A having a primary angle of 120°, the secondary sensing segment 311b defines a secondary sector 310B having a secondary angle of 120°, and the tertiary sensing segment 311c defines a tertiary sector 310C having a tertiary angle of 120°. The second sensor 312 encircles the first sensor 311, as was described in relation to FIG. 2A. The provision of a tertiary sensing segment 311c increases the sensing sensitivity of the sensor assembly 310, whereby the location of liquid can be narrowed down/distinguished to a greater detail than by providing two sensing segments. The provision of a third sensing segment 311c can increase the complexity of the first sensor 311, and as such is to be considered a trade-off between sensing sensitivity and complexity, e.g., in manufacturing.

FIG. 2C illustrates an exemplary sensor assembly 320 similar to the ones illustrated in FIGS. 2A and 2B. The sensor assembly 320 of FIG. 2C differs from the sensor assemblies 300,310 of FIGS. 2A and 2B by the first sensor 321 comprising four sensing segments, a primary sensing segment 321a, a secondary sensing segment 321b, a tertiary sensing segment 321c, and a quaternary sensing segment 321d. Each of the four sensing segments defines a sector having a central angle of 90°. The primary sensing segment 321a defines a primary sector 320A having a primary angle of 90°, the secondary sensing segment 321b defines a secondary sector 320B having a secondary angle of 90°, the tertiary sensing segment 321c defines a tertiary sector 320C having a tertiary angle of 90°, and the quaternary sensing segment 321d defines a quaternary sector 320D having a quaternary angle of 90°. The second sensor 322 encircles the first sensor 321, as was described in relation to FIGS. 2A and 2B. The provision of a quaternary sensing segment 321d increases the sensing sensitivity of the sensor assembly 320, whereby the location of liquid can be narrowed down/ distinguished to a greater detail when by providing two or three sensing segments. The provision of a quaternary sensing segment 321d can increase the complexity of the first sensor 321, and as such is to be considered a trade-off between sensing sensitivity and complexity, e.g., in manufacturing.

In general, increasing the number of sensing segments of the first sensor increases the sensing sensitivity of the ostomy system. By sensing sensitivity is meant the ability of the ostomy system to accurately indicate where (in which direction/sector) about the stoma liquid (output) is present.

To reduce the complexity of the sensor assembly, the ostomy appliance according to embodiments of the invention is provided with a first sensor divided into sensing segments, a continuous circular second sensor, and an ability—by means of processing power—to indicate/predict a site of leakage based on readings/detections from the sensors. Thereby, in particular the complexity of the second sensor is reduced, without greatly compromising the given sensing sensitivity of the ostomy system. Details on the ability of the ostomy system to indicate/predict a site of leakage is described in more detail in relation to FIGS. 3A and 3B below.

Figure 3A:
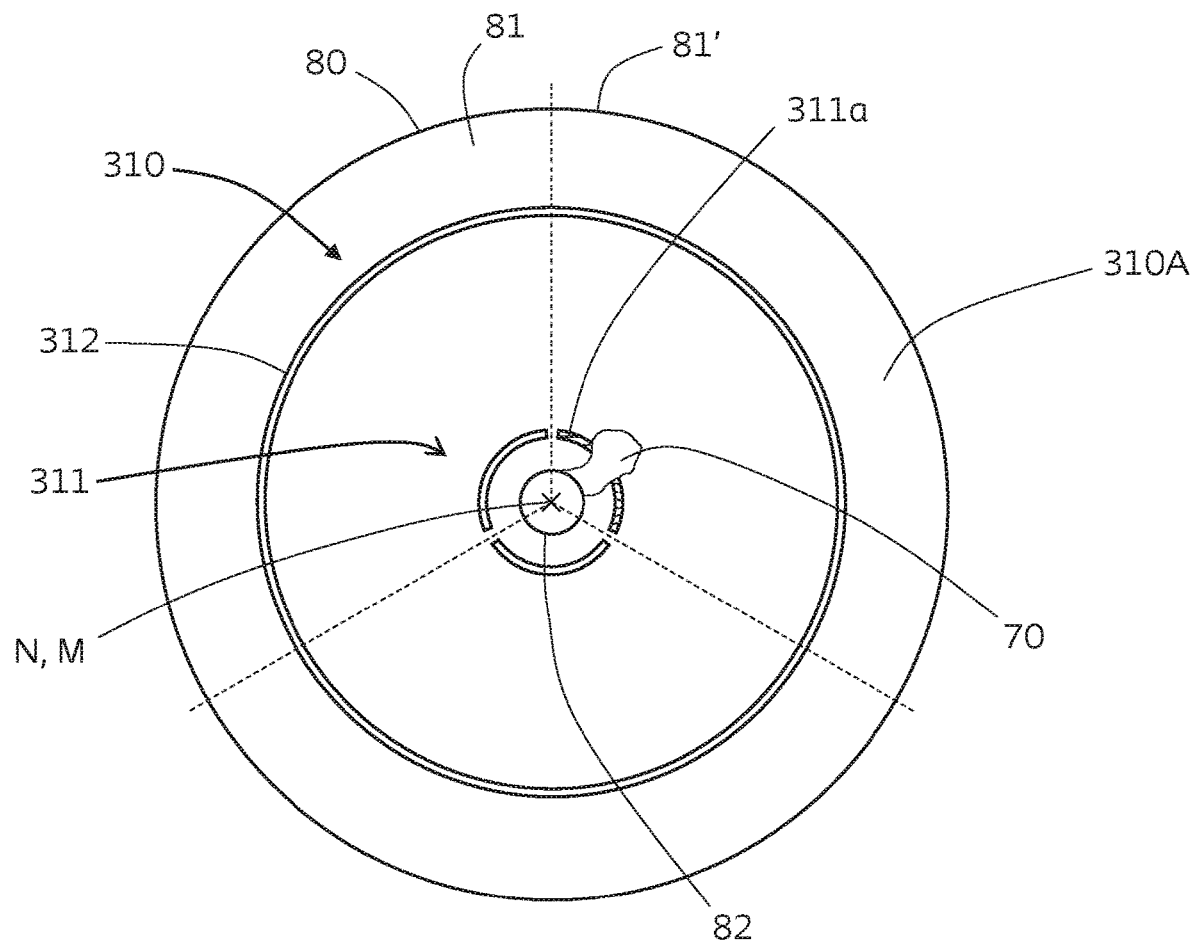
FIG. 3A illustrates a view of a proximal surface of a first adhesive layer and an exemplary sensor assembly of an ostomy system according to an embodiment of the invention.

FIG. 3A illustrates a view of the proximal surface 81 of a first adhesive layer 80 and an exemplary sensor assembly 310 of an ostomy appliance of the ostomy system. The exemplary sensor assembly 310 highlights the relative arrangement of the sensors 311,312 and their arrangement relative to the first adhesive layer 80, but FIG. 3A is not necessarily intended to illustrate specific embodiments of the sensors or means for communicating with said sensors. The sensor assembly 310 is arranged to facilitate detection of liquid (output) on the proximal surface 81. Thus, the specific arrangement of the sensor assembly 310 relative to the first adhesive layer 80 as illustrated in FIG. 3A is of minor importance, whereas the main purpose is to describe the principles of the ostomy system according to an embodiment of the invention. Thus, the sensor assembly 310 can both be arranged on the proximal surface 81 or a distal surface of the first adhesive layer 80.

The first adhesive layer 80 comprises a stomal opening 82 adapted to surround a stoma of a user (not shown). The stomal opening 82 comprises a centre point N aligned with a centre point of the sensor assembly M such that the first sensor 311 and the second sensor 312 can be arranged circularly and concentric about the stoma. Exemplary liquid/ output 70 emanating from the stoma is illustrated to highlight the working principles of the ostomy system, as will be described below. The liquid 70 is arranged in the interface between the perisomal skin area and the proximal surface 81 of the first adhesive layer 80. Thus, it is desired to alert the user, since such liquid can cause skin damage and/or leakage if it propagates to the periphery/edge 81' of the first adhesive layer 80.

At first, the liquid/output is detected at the primary sensing segment 311a (hatched to illustrate the detection), indicating that the output/liquid 70 is within the first sector 310A extending from 0° to 120°. The exact pattern of the liquid/output 70 cannot immediately be resolved by the primary sensing segment 311a—only that the liquid/output 70 is somewhere within the first sector 310A, and that the liquid has propagated the distance from the stomal opening 82 to the primary sensing segment 311a. After a certain amount of time, the second sensor 312 detects a presence of liquid/output, as is illustrated in FIG. 3B.

Figure 3B:
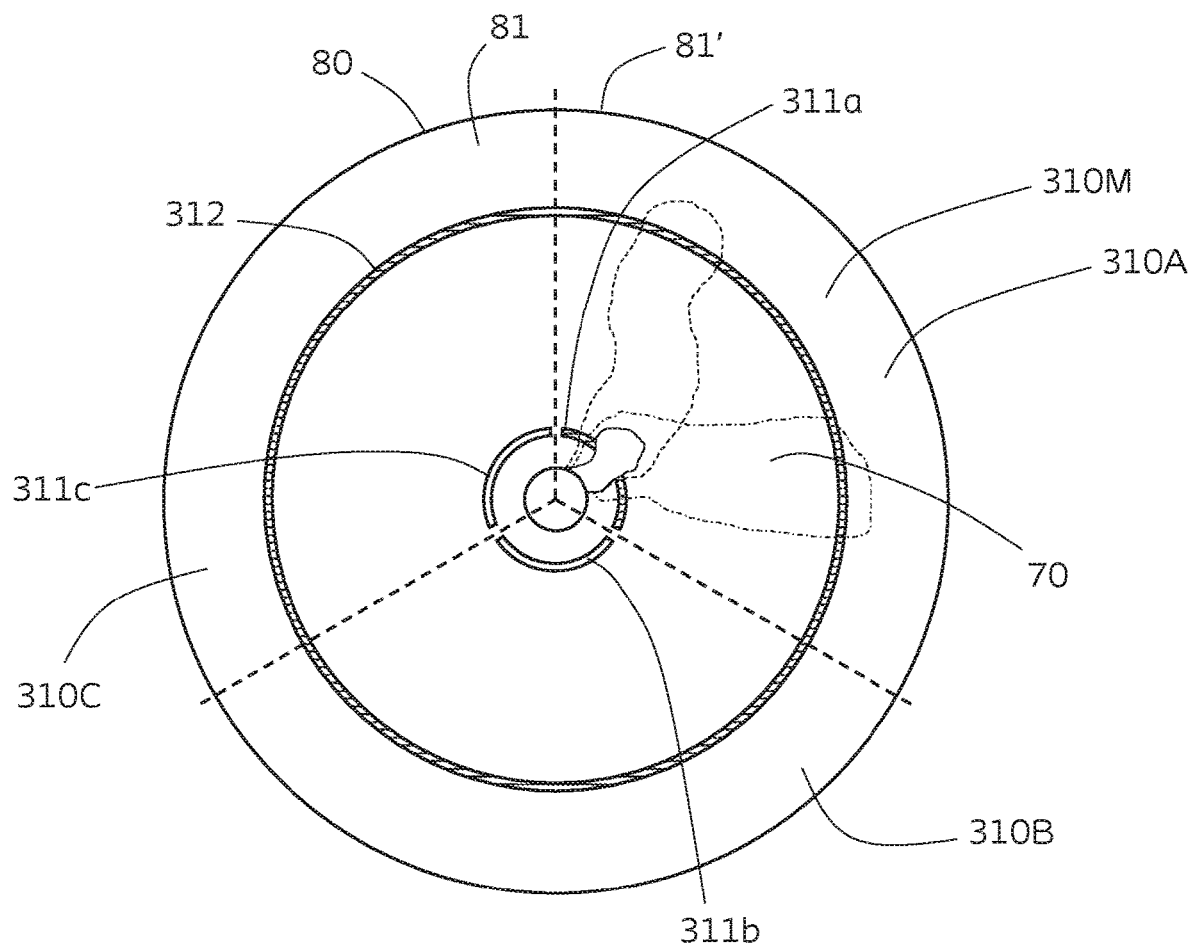
FIG. 3B illustrates a view of a proximal surface of a first adhesive layer and an exemplary sensor assembly of an ostomy system according to an embodiment of the invention.

FIG. 3B illustrates the situation where the liquid/output 70 from FIG. 3A has propagated the distance from the first sensor 311 to the second sensor 312. The pattern of the liquid/output 70 is inherently unknown due to a finite sensing sensitivity of the sensor assembly 310. However, for the purpose of discussing the working principles of the ostomy system, two equally possible patterns of liquid/output 70 is illustrated by hatched lines. Both of these patterns reside completely within the primary sector 310A, and both has been detected by the second sensor 312.

Due to the second sensor 312 being continuous about and enclosing the first sensor 311, a detection of liquid/output 70 at the second sensor 312 cannot immediately be attributed a certain sector. Instead, a detection of liquid/output 70 at the second sensor 312 can be a result of liquid/output at any point about the stoma. However, by applying the processing power of a monitor device—being part of the ostomy system and coupled to the sensor assembly 310—to the established facts of the described situation, certain aspects can be derived. The established facts of the situation described and depicted in FIG. 3B include that;

only the primary sensing segment 311a—defining the primary sector 310A—of the first sensor 311 has detected liquid/output 70, and the second sensor 312 has detected liquid 70.

From these facts, the monitor device is configured to determine a main sector of the sensor assembly. A main sector is a (volatile) sector of the sensor assembly comprising the sector(s) wherein liquid has been detected by a sensing segment(s). By volatile is meant that the main sector is a sector determined by the monitor device and can change if conditions change (e.g., if additional detections of liquid/output occur at additional sensing segments of the first sensor 311). In the situation depicted in FIG. 3B, the main sector 310M is identical to the primary sector 310A since liquid/output 70 has only been detected at the primary sensing segment 311a. If liquid/output had also been detected at the secondary sensing segment 311b and/or tertiary sensing segment 311c, the main sector would comprise the secondary 310A and/or tertiary sector 310C as well.

Following the determination of the main sector 310M, the monitor device is configured to indicate a site of leakage from the ostomy appliance. Indicating a site of leakage can be considered a prediction and/or approximation based on the established facts given above (dependent on the situation)—i.e., at least on the main sector 310M. The ostomy appliance is the ostomy appliance embodying the ostomy system as disclosed, e.g., a base plate comprising the first adhesive layer 80. Thus, by leakage is meant the situation where output exits the interface formed between the proximal surface 81 of the first adhesive layer 80 of the base plate and/or a sensor patch attached to a base plate and a skin surface of a user. The indication of the site of leakage is based on at least the main sector 310M determined by the monitor device. Thus, based on the main sector 310M, the monitor device is configured to indicate the site of leakage to be along the periphery/edge 81' of the first adhesive layer 81 arranged/residing within the main sector 310M—here, the primary sector 310A. In embodiments, indicating the site of leakage comprises transmitting an associated signal to an accessory device comprising a graphical user interface. Thereby, the accessory device can visualize the site of leakage as indicated by the monitor device. The site of leakage represents the most probable site of an imminent leakage, and as such constitutes a prediction or forecast.

As previously discussed, an accuracy can be assigned to the site of leakage, due to the site of leakage being a prediction/forecast. One parameter affecting the accuracy of the site of leakage is the time delay between liquid was detected at the first sensor and liquid was detected at the second sensor. Thus, the time delay represents the speed of propagation. A high speed of propagation increases the probability for the leakage to occur in the main sector—i.e., the accuracy of the site of leakage can be assigned to be high. For example, a high speed of propagation can be the result of poor adhesion of the first adhesive layer to the peristomal skin area, or the result of a large amount of output entering the interface. A low speed of propagation increases the probability that the liquid enters neighbouring sectors—e.g., without being detected by additional sensing segments. Thus, a low speed of propagation can result in a low accuracy to be assigned to the indicated site of leakage. Thus, the monitor device can be configured to determine/calculate the time delay and indicate the site of leakage based on both the main sector and such time delay. For example, indicating the site of leakage based on the main sector and the time delay can involve visualizing the main sector in a graphical user interface combined with a statement (e.g., number or colour code) depicting the accuracy of the main sector.

Figure 4:
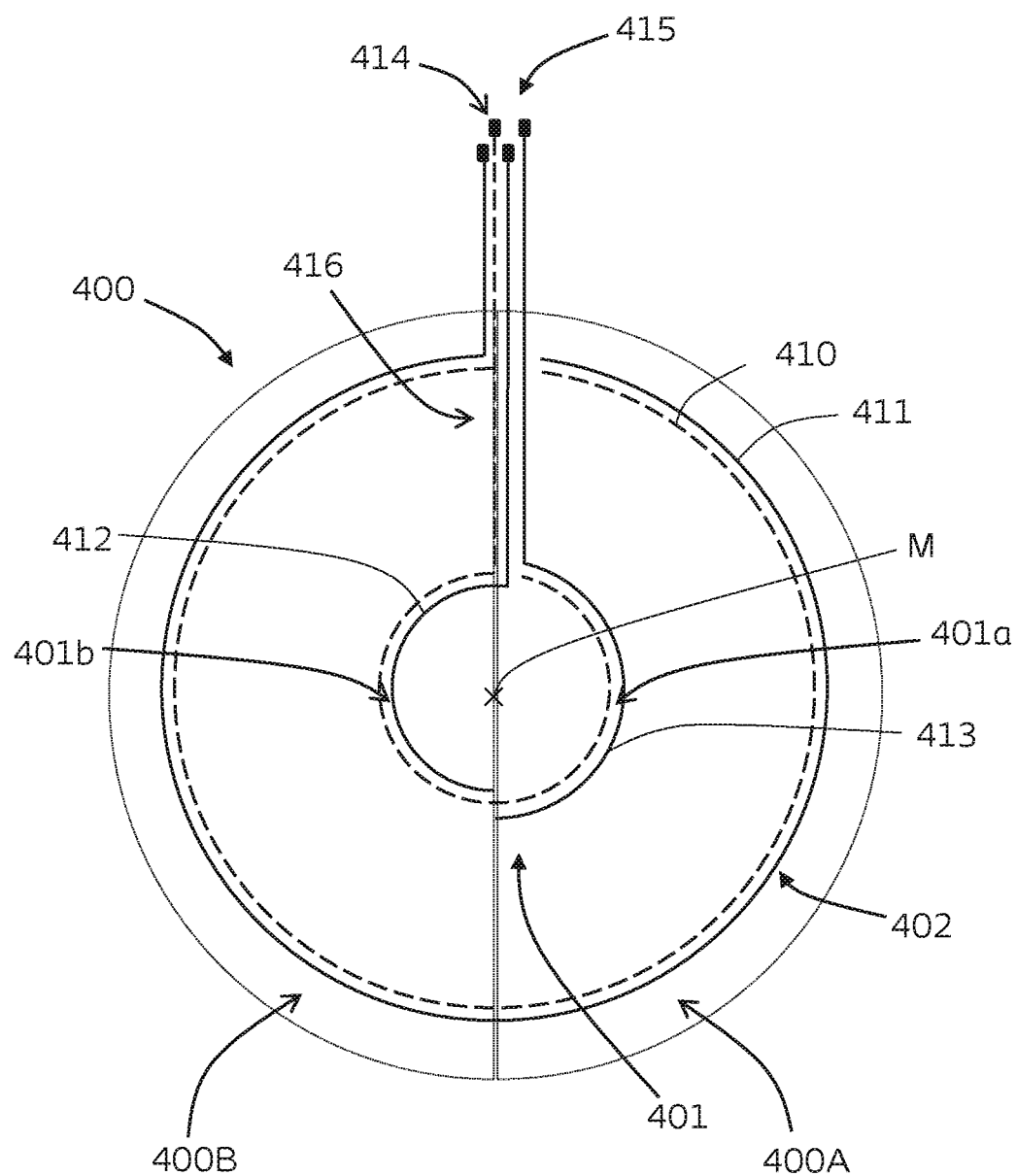
FIG. 4 illustrates an exemplary electrode assembly for a sensor assembly of an ostomy system according to an embodiment of the invention.

FIG. 4 illustrates an exemplary electrode assembly 400 for a sensor assembly of an ostomy system according to an aspect of the invention. The electrode assembly 400 comprises a first sensor 401 encircling a centre point M and a second sensor 402 encircling the first sensor 401. The second sensor 402 and the first sensor 401 are concentric. The first sensor 401 comprises a first sensing segment 401a and a second sensing segment 401b, each of which covering an angle of 180°. Thus, the electrode assembly 400 provides the sensor assembly with a primary sector 400A and a secondary sector 400B (highlighted by dotted half-moon (180°) shapes to increase the intelligibility), each of which being defined by a primary and a secondary angle of 180° each, and the extremities of the electrodes forming each of the sensing segments of the first sensor 401.

The electrode assembly 400 comprises a ground electrode 410 (dashed to increase intelligibility) and a first electrode 411, a second electrode 412, and a third electrode 413. The ground electrode 410 is a common ground for each of the three electrodes 411,412,413 in the specific embodiment. However, in embodiments, a separate ground electrode is provided for each of the additional electrodes. The first electrode 411 and the ground electrode 410 forms the second sensor 402. Thus, second sensor 402 comprises an electrode pair comprising the first electrode 411 and the ground electrode 410. The second electrode 412 and the ground electrode 410 forms the primary sensing segment 401a of the first sensor 401. Thus, the primary sensing segment 401a of the first sensor 401 comprises an electrode pair comprising the second electrode 412 and the ground electrode 410. The third electrode 413 and the ground electrode 410 forms the secondary sensing segment 401b of the first sensor 401. Thus, the secondary sensing segment 401b of the first sensor 401 comprises an electrode pair comprising the third electrode 413 and the ground electrode 410. In embodiments, the first sensor comprises three or more sensing segments. For example, a tertiary sensing segment can be provided by the addition of a fourth electrode, such that the tertiary sensing segment comprises an electrode pair comprising the fourth electrode and the ground electrode.

Other configurations of the electrodes are foreseen within the invention, such as two electrodes selected from the first, second, and third electrode can constitute an electrode pair.

The shape of the primary 401a and secondary sensing segment 401b each resembles an arc of a circle, such that the sensing segments are arranged equidistantly from the centre point M.

The electrodes 410,411,412,413 extend into a monitor interface 415. The monitor interface 415 comprises terminals 414 for forming electrical connections with terminals of a monitor device couplable to the electrode/sensor assembly. It is appreciated that the part 416 of the electrodes extending into the monitor interface 415 is negligible in relation to the angular extent of the sensing segments, i.e., the part 415 takes up merely a minor sector negligible when considering the (sum of the) central angles of the primary 400A and secondary 400B sectors, and/or additional sectors.

A monitor device (not shown) connectable to the sensor assembly and hence the electrode assembly 400 can be configured to measure the resistance/conductance across an electrode pair. Thereby, changes in resistance can be attributed changes in moisture content in a first adhesive layer, when the sensor assembly is arranged appropriately on/in the first adhesive layer, or the changes in resistance can be indicative of presence of liquid, e.g., through detecting a short-circuit across the electrode pair due to the liquid forming a liquid path of low resistance across the electrode pair.

Figure 5:
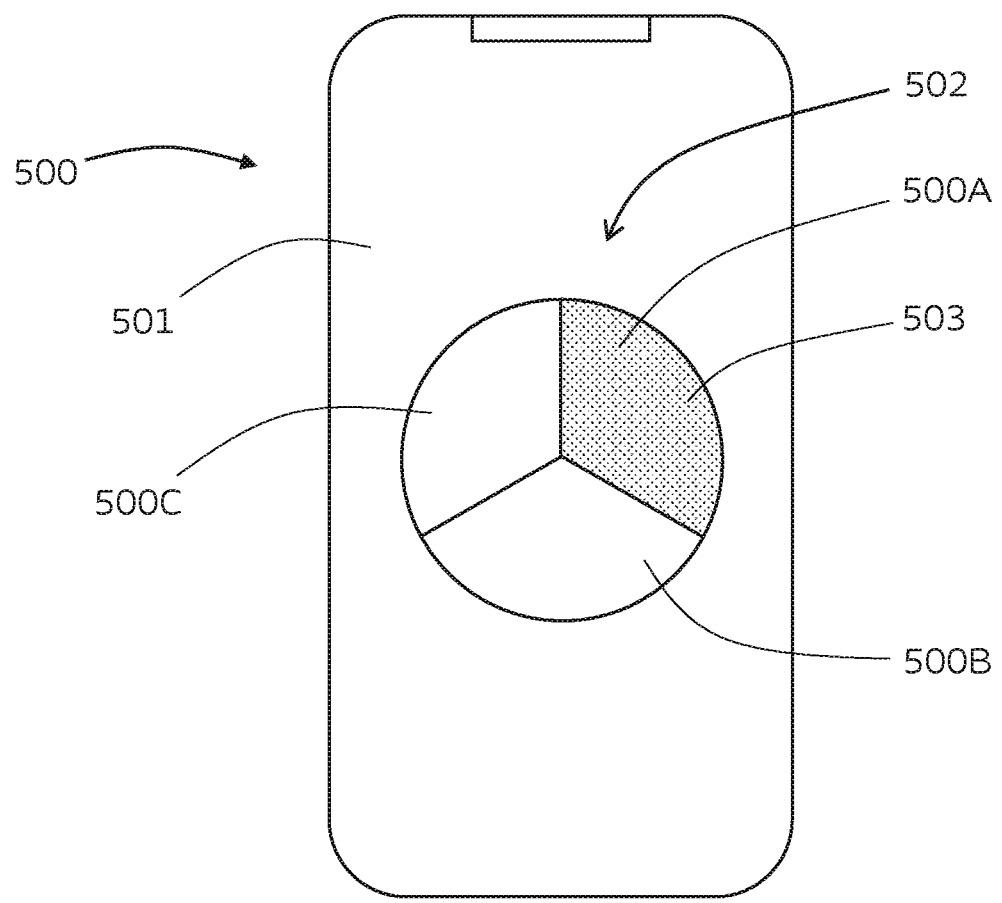
FIG. 5 illustrates an accessory device in communication with a monitor device of an ostomy system.

FIG. 5 illustrates an accessory device 500 (smartphone) comprising a graphical user interface 501. The monitor device of the ostomy system as disclosed can be configured to communicate with the accessory device, such as to display content 502 pertaining to the ostomy/ostomy system on the graphical user interface 501. For example, the content 502 is displayed in an app stored on the accessory device. The content 502 illustrated in FIG. 5 comprises a visualization of the ostomy system disclosed, where the ostomy system comprises a sensor assembly comprising three sectors, visualized by the corresponding sectors 500A,500B, 500C. Thereby, the user can easily access data derivable from the sensors of the sensor assembly. In particular, the visualization of FIG. 5 comprises an indication of a site of leakage 503. The indicated site of leakage 503 is in the primary sector 500A of the ostomy system (hence the shaded area)—i.e., the part of the periphery of the first adhesive layer residing within the primary sector 500A (see e.g., FIG. 3B). Thereby, the user is notified that a leakage is imminent within the primary sector 500A, and he/she can take remedying actions, e.g., by changing the base plate and/or sensor patch incorporating the ostomy system.

Figure 6:
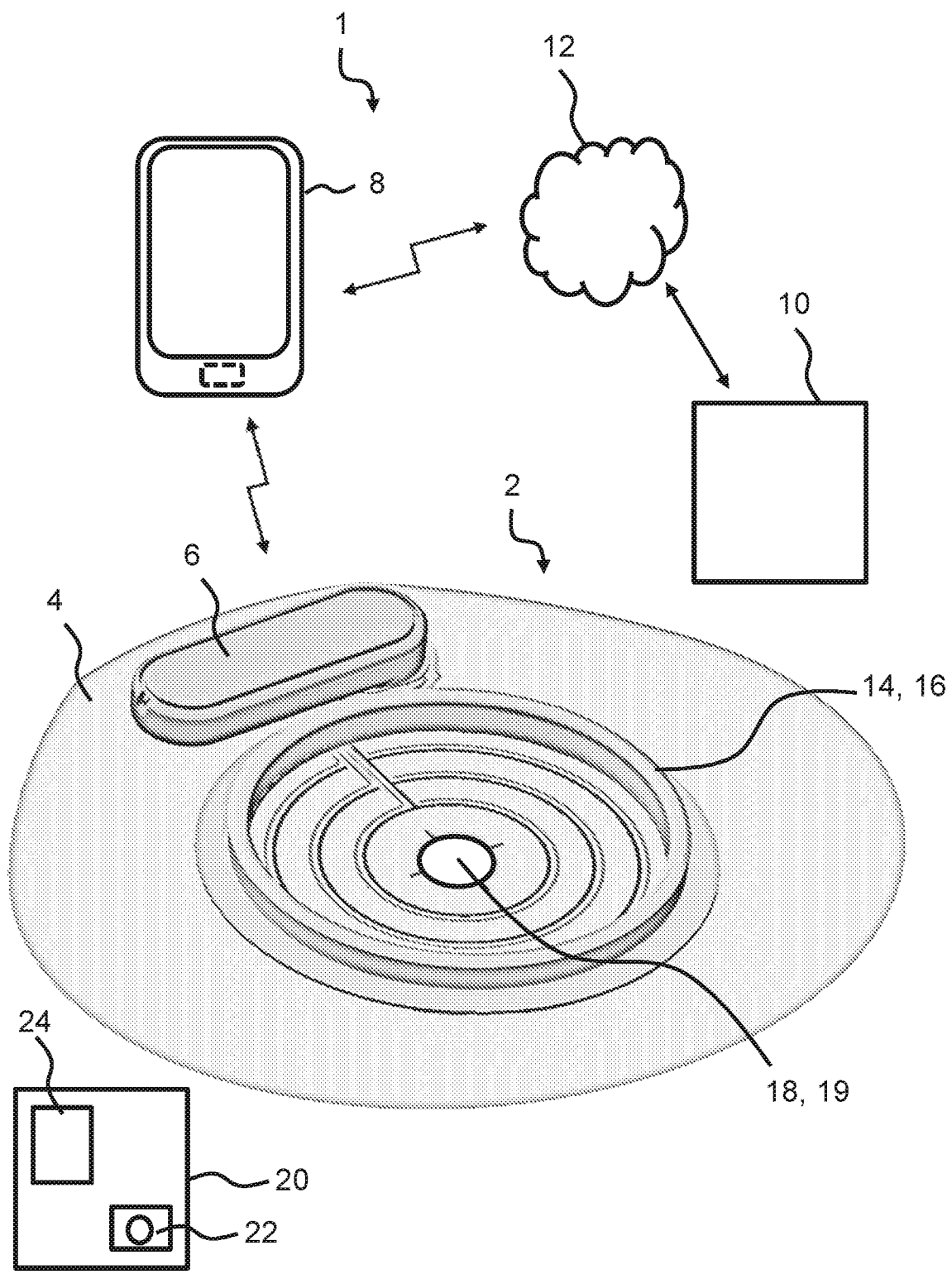
FIG. 6 illustrates an exemplary ostomy system.

FIG. 6 illustrates an exemplary ostomy system 1. The ostomy system 1 comprises an ostomy appliance 2 including a base plate 4. The base plate 4 is adapted to support an ostomy pouch (not shown). The base plate 4 comprises a first adhesive layer and a sensor assembly. Further, the ostomy system 1 comprises a monitor device 6 and an accessory device 8 (mobile telephone/smartphone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g., via network 12. The server device 10 can be operated and/or controlled by the ostomy appliance manufacturer and/or a service centre. Ostomy data or parameter data based on the ostomy data are obtained from electrodes/sensors of the sensor assembly of the ostomy appliance 2 with the monitor device 6. The monitor device 6 processes the ostomy data and/or parameter data based on the ostomy data. Based on the processed ostomy data, the monitor device 6 may determine what monitor data that are transmitted to the accessory device 8. In the illustrated ostomy system, the accessory device 8 is a mobile phone, however the accessory device 8 can be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate 4 has a stomal opening 18 with a centre point 19. The size and/or shape of the stomal opening 18 is typically adjusted by the user or nurse before application of the ostomy appliance to accommodate the user's stoma.

The ostomy system 1 optionally comprises a docking station 20 forming an alternative/additional accessory device of the ostomy system 1. The docking station 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 7:
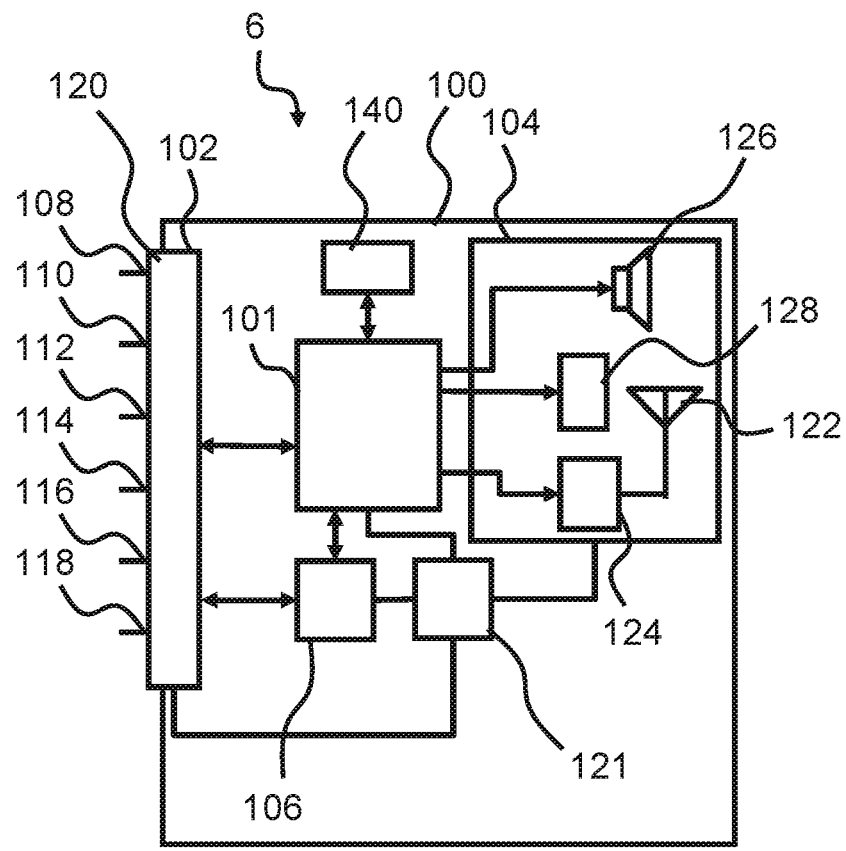
FIG. 7 illustrates an exemplary monitor device of the ostomy system.

FIG. 7 is a schematic block diagram of an exemplary monitor device. The monitor device 6 comprises a monitor device housing 100, a processor 101, and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g., ostomy appliance 2. The first interface 102 comprises a plurality of terminals for forming electrical connections with respective terminals of the ostomy appliance 2 (base plate 4, in particular the sensor assembly of the ostomy system incorporated into the base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e., the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g., terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user. In embodiments, the monitor device 6 comprises a 3-axis accelerometer 140 connected to the processor 101.

The processor 101 is configured to apply a processing scheme, and the first interface 102 (appliance interface) is configured for collecting ostomy data from the sensor assembly of the ostomy system coupled to the first interface, the ostomy data comprising ostomy data pertaining to detections of liquid at sensors of the sensor assembly. The ostomy data comprises at least first ostomy data from a first sensor of the sensor assembly and second ostomy data from a second sensor of the sensor assembly. The ostomy data can be stored in the memory 106 and/or processed in the processor 101 in order to obtain parameter data. The parameter data can be stored in the memory 106. The processor 101 is configured to apply a processing scheme, wherein to apply a processing scheme comprises calculating parameters based on input from the sensors, where parameters include indication of a site of leakage and/or a time delay as previously discussed. The processor 101 can be configured to obtain first, second and third parameter data based on respective first, second and third ostomy data. To apply a processing scheme can comprise to determine an operating state of the ostomy system, in particular the base plate and/or the sensor patch incorporating the first adhesive layer and the sensor assembly. An operating state is indicative of an acute leakage risk in a sector of the ostomy appliance, such as the main sector comprising the sectors wherein liquid has been detected by the respective sensing segments. The monitor device 6 is configured to, in accordance with a determination that the site of leakage is most likely within the main sector, transmit a main signal comprising the indication of a site of leakage to be within the main sector via the second interface. The second interface can be in (wireless) communication with an accessory device, such as to provide the indication of the site of leakage in a graphical user interface of the accessory device.

Figure 8:
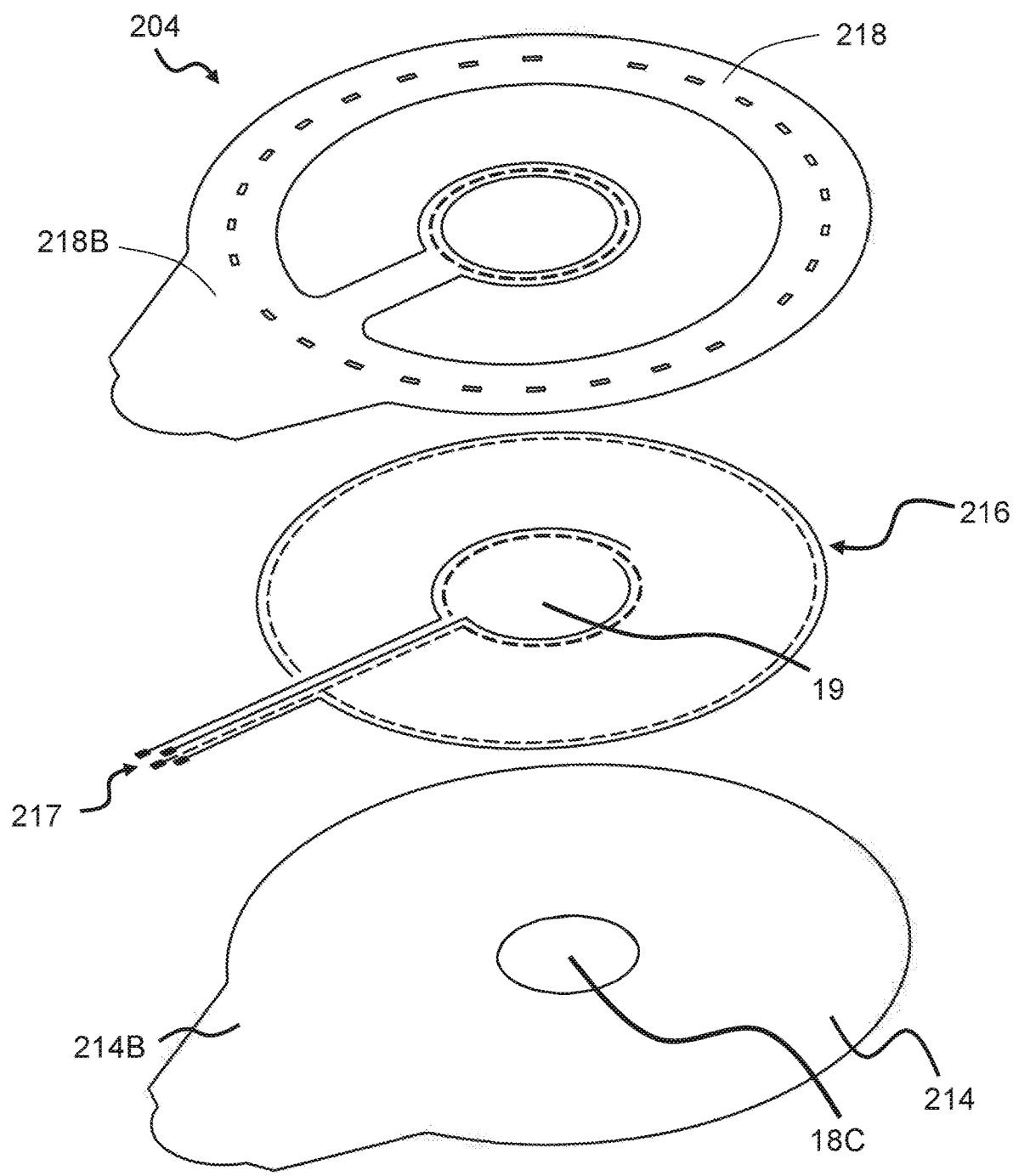
FIG. 8 illustrates an exploded view of an exemplary sensor assembly.

FIG. 8 illustrates an exploded view of an exemplary sensor assembly 204 of an ostomy system according to an aspect of the invention. The sensor assembly 204 has a distal side and a proximal side, the proximal side being configured to be attached to a distal side of an adhesive layer, such as a first adhesive layer of a base plate or a sensor patch. The sensor assembly 204 comprises a support layer 214 with a proximal surface 214B and an electrode assembly 216 arranged on the proximal side of the support layer 214 and including a ground electrode, a first electrode, a second electrode, and a third electrode, wherein each electrode has a respective connection part 217 for connecting the electrodes 216 to respective terminal elements of the monitor interface. The electrode assembly 216 form sensors for detection liquid. The electrodes 216 are positioned and/or formed on a proximal side 214B of the support layer 214. Further, the sensor assembly 204 comprises a masking element 218 with a proximal surface 218B and a distal surface and configured to insulate electrode parts of electrodes of the electrode assembly 216 from the first adhesive layer of the base plate and/or the sensor patch. The masking element 218 covers or overlap with parts of the electrodes of the electrode assembly 216 when seen in the axial direction. It is envisioned that the electrodes can be provided in a plurality of different layouts without departing from the spirit and scope of the claimed invention.

A base plate suitable for incorporating the sensor assembly illustrated in FIG. 8 comprises a first adhesive layer having a stomal opening. During use, a proximal surface of the first adhesive layer adheres to the user's skin in the peristomal area and/or to additional seals, such as sealing paste, sealing tape and/or sealing ring. The base plate optionally comprises a second adhesive layer, also denoted rim adhesive layer, with a stomal opening. The sensor assembly is arranged between the first adhesive layer and the second adhesive layer, i.e. on a distal surface of the first adhesive layer. The sensor assembly comprises a support layer with stomal opening and electrodes of an electrode assembly formed on a proximal surface of the support layer. The base plate comprises a release liner that is peeled off by the user prior to applying the base plate on the skin. The base plate comprises a top layer with a stomal opening and a coupling ring for coupling an ostomy pouch to the base plate. The top layer is a protective layer protecting the second adhesive layer from external strains and stress during use.

The base plate comprises a monitor interface. The monitor interface is configured for electrically and/or mechanically connecting the ostomy appliance (base plate) to a monitor device. The monitor interface of the base plate comprises a coupling part for forming a mechanical connection, such as a releasable coupling between the monitor device and the base plate. The coupling part is configured to engage with a coupling part of the monitor device for releasably coupling the monitor device to the base plate. Further, the monitor interface of the base plate comprises a plurality of terminal elements respectively forming a plurality of terminals for forming electrical connections with respective terminals of the monitor device. The coupling part and the terminals form a first connector of the base plate. The base plate can comprise a first intermediate element on the proximal side of the electrode assembly. The first intermediate element is arranged between the terminal elements forming terminals and the first adhesive layer. The first intermediate element covers the terminal elements forming terminals of the base plate when seen in the axial direction and protects the first adhesive layer from mechanical stress from the terminal elements of the base plate.

Some parts of the base plate described can be provided as a separate sensor patch to be applied to an existing base plate, e.g., comprising one or more of the components as described, such as to provide a base plate like the base plate as described. For example, a sensor patch can comprise a sensor assembly, a first connector, a first intermediate element, a first adhesive layer and a release liner. Additionally, the sensor patch can also comprise a second adhesive layer and/or a top layer. It may be envisioned that the user can provide a hole in layers of the base plate whereto the sensor patch is to be applied, to allow for the first connector of the sensor patch to protrude through layers of the base plate whereto the sensor patch is applied. Alternatively, the sensor patch can be applied to the base plate such that the first connector is positioned outside the periphery of the base plate.

Although particular features have been shown and described, it will be understood that they are not intended to limit the claimed invention, and it will be made obvious to those skilled in the art that various changes and modifications may be made without departing from the spirit and scope of the claimed invention. The specification and drawings are accordingly to be regarded in an illustrative rather than restrictive sense. The claimed invention is intended to cover all alternatives, modifications, and equivalents.

The invention claimed is:

1. An ostomy system configured to predict a site of leakage from an ostomy appliance, the ostomy system comprising:
    an ostomy appliance comprising:
        a first adhesive layer having a distal side including a distal surface and a proximal side including a proximal surface, the proximal surface being configured for attachment to the skin surface of a user, the first adhesive layer having a stomal opening with a centre point, and
        a sensor assembly arranged on the distal side of the first adhesive layer, the sensor assembly comprising:
            a first sensor at least partly encircling the centre point, and a second sensor at least partly encircling the first sensor, the first sensor and the second sensor being arranged to facilitate detection of liquid on the proximal surface of the first adhesive layer, the first sensor comprising at least a primary sensing segment arranged in a primary sector of the sensor assembly, and
            a secondary sensing segment arranged in a secondary sector of the sensor assembly; and
    a monitor device,
        wherein the monitor device is configured to detect liquid at the primary sensing segment and/or at the secondary sensing segment of the first sensor, and to detect liquid at the second sensor, and wherein the monitor device is further configured to determine a main sector of the sensor assembly comprising the primary and/or secondary sector wherein liquid has been detected by the primary and/or secondary sensing segment, respectively, and indicate a site of leakage from the ostomy appliance based on at least the main sector.

2. The ostomy system according to claim 1, wherein the monitor device is further configured to determine a time delay between detecting liquid at the first sensor and detecting liquid at the second sensor.

3. The ostomy system according to claim 2, wherein the monitor device is configured to indicate the site of leakage based on at least the main sector and the time delay.

4. The ostomy system according to claim 2, wherein the monitor device is configured to indicate a remaining wear time of the first adhesive layer based on the main sector and/or the time delay.

5. The ostomy system according to claim 1, wherein a sensor and/or sensing segment comprises a ground electrode and a sensing electrode, and wherein the monitor device is configured to detect a short-circuit between the ground electrode and the sensing electrode, the short-circuit being indicative of liquid at the respective sensor and/or sensing segment.

6. The ostomy system according to claim 1, wherein the first sensor further comprises a tertiary sensing segment arranged in a tertiary sector of the sensor assembly.

7. The ostomy system according to claim 6, wherein the primary, secondary, and tertiary sector are non-coinciding and each spanning an angle of 120 degrees.

8. The ostomy system according to claim 6, wherein the monitor device is further configured to detect liquid at the tertiary sensing segment of the first sensor.

9. The ostomy system according to claim 1, wherein the sensor assembly comprises a third sensor arranged between the first sensor and the second sensor.

10. The ostomy system according to claim 1, wherein the monitor device is further configured to indicate a propagation of liquid based on one or more additional detections of liquid at a sensing segment of the first sensor.

11. The ostomy system according to claim 1, wherein the monitor device is configured to determine and assign an accuracy to the indicated site of leakage and/or the propagation of liquid.

12. A method, performed in a monitor device, for predicting a site of leakage from an ostomy appliance of an ostomy system, the method comprising:
    detecting liquid at a primary sensing segment and/or a secondary sensing segment of a first sensor of a sensor assembly, the primary sensing segment arranged in a primary sector of the sensor assembly and the secondary sensing segment arranged in a secondary sector of the sensor assembly, the sensor assembly arranged on a distal side of a first adhesive layer of the ostomy appliance, the first adhesive layer further including a proximal surface being configured for attachment to the skin surface of a user and a stomal opening with a centre point, the first sensor at least partly encircling the centre point,
    detecting liquid at a second sensor of the sensor assembly, the second sensor at least partly encircling the first sensor,
    determining a main sector of the sensor assembly comprising the primary and/or secondary sector wherein liquid has been detected by the primary and/or secondary sensing segment, respectively, and
    indicating a site of leakage from the ostomy appliance, the site of leakage being based on at least the main sector.

13. The method according to claim 12, wherein the method further comprises determining a time delay between detecting liquid at the primary and/or secondary sensing segment and detecting liquid at the second sensor.

14. The method according to claim 13, wherein the site of leakage is being based on at least the main sector and the time delay.

15. The method according to claim 12, wherein the method comprises indicating a propagation of liquid based on one or more additional detections of liquid at a sensing segment of the first sensor.

16. A monitor device for an ostomy system, the monitor device comprising:
    at least one processor; and
    memory storing instructions that, when executed by the at least one processor, cause the monitor device to perform a set of operations, the set of operations comprising:
        detecting liquid at a primary sensing segment and/or a secondary sensing segment of a first sensor of a sensor assembly, the primary sensing segment arranged in a primary sector of the sensor assembly and the secondary sensing segment arranged in a secondary sector of the sensor assembly, the sensor assembly arranged on a distal side of a first adhesive layer of the ostomy appliance, the first adhesive layer further including a proximal surface being configured for attachment to the skin surface of a user and a stomal opening with a centre point, the first sensor at least partly encircling the centre point,
        detecting liquid at a second sensor of the sensor assembly, the second sensor at least partly encircling the first sensor,
        determining a main sector of the sensor assembly comprising the primary and/or secondary sector wherein liquid has been detected by the primary and/or secondary sensing segment, respectively, and indicating a site of leakage from the ostomy appliance, the site of leakage being based on at least the main sector.

17. The monitor device of claim 16, wherein the monitor device is configured to indicate a remaining wear time of the first adhesive layer.

18. The monitor device of claim 16, wherein the set of operations further comprises determining a time delay between detecting liquid at the primary and/or secondary sensing segment and detecting liquid at the second sensor.

19. The monitor device of claim 18, wherein the site of leakage is being based on at least the main sector and the time delay.

20. The monitor device of claim 16, wherein the set of operations further comprises indicating a propagation of liquid based on one or more additional detections of liquid at a sensing segment of the first sensor.

* * * * *